(12) United States Patent
McPherson et al.

(10) Patent No.: US 10,477,825 B2
(45) Date of Patent: *Nov. 19, 2019

(54) COTTON VARIETY PX339054W3FE

(71) Applicant: Phytogen Seed Company, LLC, Indianapolis, IN (US)

(72) Inventors: Mustafa G. McPherson, Leland, MS (US); Joel F. Mahill, Bakersfield, CA (US); Frank C. Bordelon, Collingston, LA (US)

(73) Assignee: Phytogen Seed Company, LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/878,994

(22) Filed: Jan. 24, 2018

(65) Prior Publication Data

US 2018/0206433 A1 Jul. 26, 2018

Related U.S. Application Data

(60) Provisional application No. 62/450,771, filed on Jan. 26, 2017.

(51) Int. Cl.
*A01H 5/10* (2018.01)
*A01H 6/60* (2018.01)
*C12N 15/82* (2006.01)

(52) U.S. Cl.
CPC ............. *A01H 6/604* (2018.05); *A01H 5/10* (2013.01); *C12N 15/8275* (2013.01); *C12N 15/8286* (2013.01); *Y02A 40/162* (2018.01)

(58) Field of Classification Search
None
See application file for complete search history.

(56) References Cited

U.S. PATENT DOCUMENTS

2015/0150208 A1* 6/2015 McPherson .............. A01H 5/10
800/260

OTHER PUBLICATIONS

Dow AgroSciences Australia, Risk assessment and risk management plan, DIR 040/2003, Nov. 2003.*

* cited by examiner

*Primary Examiner* — Mykola V. Kovalenko

(57) ABSTRACT

The disclosure relates to a cotton variety, designated PX339054W3FE, the plants and seeds of the cotton variety PX339054W3FE, methods for producing a cotton plant, either varietal or hybrid, produced by crossing the cotton variety PX339054W3FE with itself or with another cotton plant, hybrid cotton seeds and plants produced by crossing the variety PX339054W3FE with another cotton variety or plan, methods for producing a cotton plant containing in its genetic material one or more transgenes, and the transgenic cotton plants produced by that method. This disclosure also relates to cotton varieties derived from cotton variety PX339054W3FE, to methods for producing other cotton varieties derived from cotton variety PX339054W3FE, and to the varieties derived by the use of those methods.

18 Claims, No Drawings

COTTON VARIETY PX339054W3FE

This application claims the benefit of U.S. Provisional Application No. 62/450,771 which was filed in the U.S. Patent and Trademark Office on Jan. 26, 2017, the entire disclosure of which is hereby incorporated by reference.

FIELD OF THE INVENTION

This invention is in the field of cotton breeding.

BACKGROUND OF THE INVENTION

Cotton (*Gossypium* spp.) is the world's most important textile fiber crop and is one of the world's most important oilseed crops. Cotton plants provide a source of human food, livestock feed, and raw material in industry. Cotton seed is pressed for cooking oil and the residual cottonseed oil meal is used for animal feed. Industrial uses of cotton include candle wicks, twine, paper and a multitude of fabric products.

The genus *Gossypium* is very large, currently containing more than 50 species. Two tetraploid species of *Gossypium* have spinnable seed fibers called lint. These two species are *G. hirsutum* (referred to as American Upland cotton) and *G. barbadense* (referred to as Pima cotton).

The goal of a cotton breeder is to improve a cotton plant's performance and therefore, its economic value by combining various desirable traits into a single plant. Improved performance is manifested in many ways. Higher yields of cotton plants contribute to increased lint fiber production, more profitable agriculture and lower cost of products for the consumer. Improved plant health increases the yield and quality of the plant and reduces the need for application of protective chemicals. Adapting cotton plants to a wider range of production areas achieves improved yield and vegetative growth. Improved plant uniformity enhances the farmer's ability to mechanically harvest cotton.

Cotton is a dicot plant with perfect flowers, i.e., cotton has male, pollen-producing organs and separate female, pollen receiving organs on the same flower. The cultivated cotton flower is surrounded by three triangular bracts forming what is commonly known as squares. The flower contains an open corolla with five petals, a staminal column bearing clusters of stamens and forming a tube that encloses the style. The compound pistil consists of three to five carpels with stigmas protruding above the anthers. The ovary develops into a three- to five-loculed capsule or boll. From seven to nine seeds are set within each lock or locule. On the day preceding anthesis, a twisted corolla emerges from the square. On the day of anthesis, the corolla opens and pollen shedding occurs. The corolla turns red the day following anthesis and later falls from the plant. Pollination occurs with the opening of the anthers and shedding of pollen on the stigma or with the deposit of pollen on the stigma by insects.

Because cotton has both male and female organs on the same flower, cotton breeding techniques take advantage of the plant's ability to be bred by both self-pollination and cross-pollination. Self-pollination occurs when pollen from the male organ is transferred to a female organ on the same flower on the same plant. Self-incompatibility is a form of infertility caused by the failure of cotton plants with normal pollen and ovules to set seed due to some physiological hindrance that prevents fertilization. Self-incompatibility restricts self-pollination and inbreeding and fosters cross-pollination. Cross-pollination occurs when pollen from the male organ on the flower of one plant is transferred to a female organ on the flower on a different plant.

A plant is sib-pollinated (a type of cross-pollination) when individuals within the same family or line are used for pollination (i.e. pollen from a family member plant is transferred to the stigmas of another family member plant). Self-pollination and sib-pollination techniques are traditional forms of inbreeding used to develop new cotton varieties, but other techniques exist to accomplish inbreeding. New cotton varieties are developed by inbreeding heterozygous plants and practicing selection for superior plants for several generations until substantially homozygous plants are obtained. During the inbreeding process with cotton, the vigor of the lines decreases and after a sufficient amount of inbreeding, additional inbreeding merely serves to increase seed of the developed variety. Cotton varieties are typically developed for use in the production of hybrid cotton lines.

Natural, or open pollination, occurs in cotton when bees or other insects transfer pollen from the anthers to the stigmas and can include both self- and cross-pollination. Such pollination is accomplished almost entirely by the bees or other pollinating insects as the pollen is heavy and sticky and accordingly, interplant transfer of pollen by the wind is of little importance. Vigor is restored when two different varieties are cross-pollinated to produce the first generation ($F_1$) progeny. A cross between two defined substantially homozygous cotton plant varieties always produces a uniform population of heterozygous hybrid cotton plants and such hybrid cotton plants are capable of being generated indefinitely from the corresponding variety cotton seed supply.

When two different, unrelated cotton parent plant varieties are crossed to produce an $F_1$ hybrid, one parent variety is designated as the male, or pollen parent, and the other parent variety is designated as the female, or seed parent. Because cotton plants are capable of self-pollination, hybrid seed production requires elimination of or inactivation of pollen produced by the female parent to render the female parent plant male sterile. This serves to prevent the cotton plant variety designated as the female from self-pollinating. Different options exist for controlling male fertility in cotton plants such as physical emasculation, genetic male sterility, cytoplasmic male sterility and application of gametocides. Incomplete removal of male parent plants from a hybrid seed production field before harvest provides the potential for unwanted production of self-pollinated or sib-pollinated seed, which can be unintentionally harvested and packaged with hybrid seed.

The development of new cotton plant varieties and hybrid cotton plants is a slow, costly interrelated process that requires the expertise of breeders and many other specialists. The development of new varieties and hybrid cotton plants in a cotton plant breeding program involves numerous steps, including: (1) selection of parent cotton plants (germplasm) for initial breeding crosses; (2) inbreeding of the selected plants from the breeding crosses for several generations to produce a series of varieties, which individually breed true and are highly uniform; and (3) crossing a selected variety with an unrelated variety to produce the $F_1$ hybrid progeny having restored vigor.

Cotton plant varieties and other sources of cotton germplasm are the foundation material for all cotton breeding programs. Despite the existence and availability of numerous cotton varieties and other source germplasm, a continuing need still exists for the development of improved germplasm because existing parent cotton varieties lose their commercial competitiveness over time. Embodiments of the present disclosure addresses this need by providing a novel cotton inbred variety designated PX339054W3FE that possesses broad adaptation and excellent yield stability in the full-maturity cotton growing regions of the US; excellent fiber properties such as micronaire, length, strength (g/tex), and fiber uniformity; the WideStrike® 3 transgenic trait comprised of three events, expressing the Cry1F, Cry1Ac and Vip3A genes, with each *Bacillus thuringiensis*-derived toxin conferring resistance to Lepidopteran insects; the Enlist™ transgenic trait conferring tolerance to 2,4-dichlorophenoxyacetic acid (2,4-D) and glufosinate herbicides; and the Roundup Ready® Flex transgenic trait, conferring tolerance to glyphosate herbicide.

PX339054W3FE contributes such characteristics to hybrids relative to other similar hybrids in the same maturity groups. To protect and to enhance yield production, trait technologies and seed treatment options provide additional crop plan flexibility and cost effective control against insects, weeds and diseases, thereby further enhancing the potential of this variety and hybrids with PX339054W3FE as a parent.

SUMMARY OF THE INVENTION

Embodiments of this disclosure relate to a cotton variety designated PX339054W3FE that includes plants and seeds of cotton variety PX339054W3FE. Further embodiments relate to lint having novel characteristics whether or not produced by the claimed cotton variety. Methods for producing cotton plants, such as cotton plant varieties, hybrid cotton plants, or other cotton plants, as by crossing cotton variety PX339054W3FE with itself or any different cotton plant are an integral part of certain embodiments, as are the resultant cotton plants including the plant parts and seeds. Other embodiments relate to methods for producing PX339054W3FE-derived cotton plants, to methods for producing male sterile PX339054W3FE cotton plants, e.g., cytoplasmic male sterile PX339054W3FE cotton plants and to methods for regenerating such plants from tissue cultures of regenerable cells as well as the plants obtained therefrom. Methods for producing a cotton plant containing in its genetic material one or more transgenes, and the transgenic cotton plants produced by that method, are also a part of further embodiments.

In one embodiment, the present disclosure relates to a seed of the cotton variety designated PX339054W3FE, or a part thereof, representative seed of the variety having been deposited under ATCC Accession No. PTA-123652. In a further aspect, the disclosure relates to a part of this seed, selected from the group consisting of hull (seed coat), germ and endosperm. In a further aspect, the disclosure relates to this seed, further comprising a coating. In a further aspect, the disclosure relates to a substantially homogenous composition of this seed.

In another embodiment, the present disclosure relates to a method for producing a seed of a cotton plant, comprising: (a) planting seed of the cotton variety designated PX339054W3FE in proximity to itself or to different seed from a same variety; (b) growing plants from the seed under pollinating conditions; and (c) harvesting the resultant seed. In a further aspect, the disclosure relates to a cotton seed produced by this method. In a further aspect, the disclosure relates to this method, further comprising pre-treating the seed before performing step (a). In a further aspect, the disclosure relates to this method, further comprising treating the growing plants or soil surrounding the growing plants with an agricultural chemical.

In another embodiment, the present disclosure relates to a cotton plant produced by growing a seed of the cotton variety designated PX339054W3FE. In a further aspect, the disclosure relates to a part of this cotton plant, selected from the group consisting of an intact plant cell, a plant protoplast, embryos, pollen, flowers, seeds, linters, fibers, pods, gossypol glands, leaves, bolls, stems, roots, root tips, and anthers. In a further aspect, the disclosure relates to fibers of this plant. In a further aspect, the disclosure relates to staples of this plant. In a further aspect, the disclosure relates to a cotton plant, or a part thereof, having all the physiological and morphological characteristics of this cotton plant. In a further aspect, the disclosure relates to a substantially homogenous population of these cotton plants. In a further aspect, the disclosure relates to this substantially homogenous population of cotton plants, wherein the population is present in a field and the field further comprises other, different cotton plants.

In another embodiment, the present disclosure relates to a method for producing a cotton plant, comprising: (a) crossing cotton variety plant PX339054W3FE, representative seed of the cultivar having been deposited under ATCC Accession No. PTA-123652, with another different cotton plant to yield progeny cotton seed. In a further aspect, the disclosure relates to this method, wherein the other, different cotton plant is a cotton variety. In a further aspect, the disclosure relates to this method, further comprising: (b) growing the progeny cotton seed from step (a) under self-pollinating or sib-pollinating conditions for about 5 to about 7 generations; and (c) harvesting resultant seed. In a further aspect, the disclosure relates to this method, further comprising selecting plants obtained from growing at least one generation of the progeny cotton seed for a desirable trait.

In another embodiment, the present disclosure relates to a method of introducing a desired trait into cotton variety PX339054W3FE, representative seed of the variety having been deposited under ATCC Accession No. PTA-123652, comprising: (a) crossing PX339054W3FE plants with plants of another cotton variety that comprise a desired trait to produce F1 progeny plants; (b) selecting F1 progeny plants that have the desired trait; (c) crossing selected progeny plants with PX339054W3FE plants to produce backcross progeny plants; (d) selecting for backcross progeny plants that comprise the desired trait and physiological and morphological characteristics of cotton variety PX339054W3FE; and (e) performing steps (c) and (d) one or more times in succession to produce the selected or higher backcross progeny plants that comprise the desired trait and all of the physiological and morphological characteristics of cotton variety PX339054W3FE listed in Table 1 as determined at the 5% significance level when grown in the same environmental conditions. In a further aspect, the disclosure relates to this method, wherein the plants of the other cotton variety comprise a desired trait selected from the group consisting of male sterility, drought tolerance, herbicide resistance, insect resistance, and resistance to bacterial, fungal and viral disease. In a further aspect, the disclosure relates to this method, further comprising using direct or indirect selection to determine whether the desired trait is present in a progeny plant.

In another embodiment, the present disclosure relates to a method for producing a cotton plant, comprising: (a) crossing a cotton plant produced by growing a seed of the cotton variety designated PX339054W3FE with another different cotton plant to produce a diploid or progeny plant; (b)

generating a haploid progeny plant from the diploid progeny plant; (c) generating a diploid plant from the haploid progeny plant; and (d) selecting the diploid cotton plant. In a further aspect, the disclosure relates to this method, wherein the haploid progeny plant is generated by culturing a haploid explant from the diploid progeny plant. In a further aspect, the disclosure relates to this method, wherein the haploid progeny plant is generated by crossing the progeny plant with another, different plant that induces haploid cotton plants. In a further aspect, the disclosure relates to this method, wherein the other, different plant is a cotton plant that comprises a haploid-inducing gene. In a further aspect, the disclosure relates to this method, wherein the diploid plant of step (c) is generated by subjecting the haploid progeny plant to a treatment that induces chromosome doubling in the cultured explant. In a further aspect, the disclosure relates to this method, wherein the diploid plant of step (c) is generated by self-pollinating the haploid progeny plant.

In another embodiment, the present disclosure relates to a method for producing a cotton plant, comprising: (a) inducing a mutation in a cotton plant produced by growing a seed of the cotton variety designated PX339054W3FE, or a part thereof; and, (b) selecting mutated cotton plants. In a further aspect, the disclosure relates to this method, wherein the mutation is artificially induced by a method selected from the group consisting of elevated temperature, long-term seed storage, tissue culture conditions, radiation, and chemical mutagenesis.

In another embodiment, the present disclosure relates to a method for producing a cotton plant variety, comprising: (a) growing first generation hybrid cotton plants having PX339054W3FE, representative seed of the variety having been deposited under ATCC Accession No. PTA-123652, as a parent cotton plant; (b) inbreeding the first generation hybrid cotton plants or crossing the first generation hybrid cotton plants with different cotton plants to yield progeny cotton seed; (c) growing the progeny cotton seed of step (b) to yield further progeny cotton seed; (d) repeating the inbreeding or the crossing and the growing steps of (b) and (c) from about 0 to about 7 times to generate cotton varietal plants. In a further aspect, the disclosure relates to a cotton plant variety produced by this method.

In another embodiment, the present disclosure relates to a method for producing cotton variety PX339054W3FE, representative seed of the variety having been deposited under ATCC Accession No. PTA-123652, comprising: (a) planting a collection of seed comprising seed of a hybrid, one of whose parents is PX339054W3FE, the collection also comprising seed of the variety PX339054W3FE; (b) growing plants from the collection of seed; (c) identifying a varietal parent plant; (d) controlling pollination in a manner that preserves the homozygosity of the varietal parent plant; and, (e) harvesting the resultant seed from the identified varietal parent plant which was pollinated to preserve its homozygosity. In a further aspect, the disclosure relates to this method, wherein step (c) comprises identifying plants with decreased vigor. In a further aspect, the disclosure relates to a method for producing a varietal cotton plant comprising: sib-pollinating plants obtained by growing the harvested resultant seed of step (e) of this method. In a further aspect, the disclosure relates to a method for producing a varietal cotton plant comprising: crossing PX339054W3FE cotton plants with cotton plants obtained by growing the hybrid seed of step (a) of this method.

In another embodiment, the present disclosure relates to a method for producing a hybrid cotton seed comprising crossing a first varietal parent cotton plant with a second varietal parent cotton plant and harvesting resultant hybrid cotton seed, wherein the first varietal cotton plant or the second varietal cotton plant is a cotton plant produced by growing a seed of the cotton variety designated PX339054W3FE.

In another embodiment, the present disclosure relates to a method for producing a hybrid cotton seed comprising the steps of: (a) planting in pollinating proximity seeds of a first and a second varietal parent cotton plants, wherein the first varietal cotton plant or the second varietal cotton plant is a cotton plant produced by growing a seed of the cotton variety designated PX339054W3FE; (b) cultivating the seeds of the first and the second varietal cotton plants into plants that bear flowers; (c) controlling the male fertility of the first or the second varietal cotton plant to produce a male sterile cotton plant; (d) allowing cross-pollination to occur between the first and second varietal cotton plants; and, (e) harvesting seeds produced on the male sterile cotton plant. In a further aspect, the disclosure relates to this method, wherein the varietal cotton plant that is the cotton plant produced by growing a seed of the cotton variety designated PX339054W3FE is a female parent. In a further aspect, the disclosure relates to this method, wherein the varietal cotton plant that is the cotton plant produced by growing a seed of the cotton variety designated PX339054W3FE is a male parent. In a further aspect, the disclosure relates to a hybrid cotton seed produced by this method. In a further aspect, the disclosure relates to a hybrid cotton plant, or parts thereof, producing by growing this hybrid cotton seed. In a further aspect, the disclosure relates to a tissue culture of regenerable cells from this hybrid cotton plant. In a further aspect, the disclosure relates to a cotton seed obtained by growing the hybrid cotton seed produced by this method and harvesting the resultant cotton seed from produced plants.

In another embodiment, the present disclosure relates to a method for producing a hybrid cotton seed comprising crossing a first varietal parent cotton plant with a second varietal parent cotton plant and harvesting the resultant hybrid cotton seed, wherein the first varietal cotton plant or the second varietal cotton plant is a progeny plant of a cross of the cotton plant produced by growing a seed of the cotton variety designated PX339054W3FE and another varietal cotton plant. In a further aspect, the disclosure relates to a hybrid cotton seed produced by this method. In a further aspect, the disclosure relates to a hybrid cotton plant, or a part thereof, produced by growing this hybrid cotton seed. In a further aspect, the disclosure relates to a cotton seed produced by growing this hybrid cotton plant and harvesting the resultant cotton seed.

In another embodiment, the present disclosure relates to an F1 hybrid seed produced by crossing the varietal cotton plant produced by growing a seed of the cotton variety designated PX339054W3FE with another, different cotton plant. In a further aspect, the disclosure relates to a hybrid cotton plant, or a part thereof, produced by growing this hybrid cotton seed. In a further aspect, the disclosure relates to this hybrid cotton seed, wherein the other, different plant is not a member of the *hirsutum* species. In a further aspect, the disclosure relates to this hybrid cotton seed, wherein the other, different plant is a member of the *barbadense* species. In a further aspect, the disclosure relates to this hybrid cotton seed, wherein the other, different plant is a member of a genus *Gossypium*. In a further aspect, the disclosure relates to this hybrid cotton seed, wherein the other, different plant is a member of the family Malvaceae.

In another embodiment, the present disclosure relates to a method for producing a PX339054W3FE-derived cotton plant, comprising: (a) crossing cotton variety PX339054W3FE, representative seed of the variety having been deposited under ATCC Accession No. PTA-123652, with a second cotton plant to yield progeny cotton seed; and (b) growing said progeny cotton seed, under plant growth conditions, to yield the PX339054W3FE-derived cotton plant. In a further aspect, the disclosure relates to a PX339054W3FE-derived cotton plant, or a part thereof, produced by this method. In a further aspect, the disclosure relates to this method, further comprising: (c) crossing the PX339054W3FE-derived cotton plant with itself or another cotton plant to yield additional PX339054W3FE-derived progeny cotton seed; (d) growing the progeny cotton seed of step (c) under plant growth conditions, to yield additional PX339054W3FE-derived cotton plants; and (e) repeating the crossing and growing steps of (c) and (d) from 0 to 7 times to generate further PX339054W3FE-derived cotton plants. In a further aspect, the disclosure relates to this method, still further comprising utilizing plant tissue culture methods and/or haploid breeding to derive progeny of the PX339054W3FE-derived cotton plant.

In another embodiment, the present disclosure relates to a tissue culture of regenerable cells from the cotton plant produced by growing a seed of the cotton variety designated PX339054W3FE. In a further aspect, the disclosure relates to this tissue culture, the cells or protoplasts of the tissue culture being from a tissue selected from the group consisting of embryos, pollen, flowers, seeds, linters, fibers, pods, gossypol glands, leaves, bolls, stems, roots, root tips, and anthers. In a further aspect, the disclosure relates to a cotton plant regenerated from this tissue culture, wherein the regenerated plant expresses all the morphological and physiological characteristics of variety PX339054W3FE.

In another embodiment, the present disclosure relates to a cotton plant with all of the physiological and morphological characteristics of cotton variety PX339054W3FE, wherein the cotton plant is produced by a tissue culture process using the cotton plant produced by growing a seed of the cotton variety designated PX339054W3FE as a starting material for the process.

In another embodiment, the present disclosure relates to a method for regenerating a cotton plant comprising the steps of: (a) culturing an explant comprising a tissue selected from the group consisting of a tissue obtained from cotton plant variety PX339054W3FE, representative seed having been deposited under ATCC Accession No. PTA-123652, an immature tissue obtained from a hybrid cotton plant having PX339054W3FE as a parent, and a PX339054W3FE-derived cotton plant; and, (b) initiating regeneration. In a further aspect, the disclosure relates to this method, wherein the explant is an immature tissue.

In another embodiment, the present disclosure relates to a cotton plant produced by growing a seed of the cotton variety designated PX339054W3FE, wherein the PX339054W3FE plant is rendered male sterile. In a further aspect, the disclosure relates to this cotton plant, wherein the male sterile PX339054W3FE plant is a cytoplasmic male sterile plant.

In another embodiment, the present disclosure relates to a method for producing a male sterile PX339054W3FE cotton plant, comprising: (a) crossing a varietal cotton plant produced by growing a seed of the cotton variety designated PX339054W3FE, with a cytoplasmic male sterile cotton plant that generates haploids; (b) identifying haploid plants; and, (c) crossing the haploid plants with the varietal cotton plant PX339054W3FE to produce male sterile PX339054W3FE cotton plants.

In another embodiment, the present disclosure relates to a cotton plant, or a part thereof, produced by growing a seed of the cotton variety designated PX339054W3FE, wherein the plant or part thereof has been transformed so that its genetic material contains one or more transgenes operably linked to one or more regulatory elements. In a further aspect, the disclosure relates to a method for producing a cotton plant that contains in its genetic material one or more transgenes, comprising crossing this cotton plant with either a second plant of another cotton variety, or a non-transformed cotton plant of the variety PX339054W3FE, so that the genetic material of the progeny that result from the cross contains the transgene(s) operably linked to a regulatory element. In a further aspect, the disclosure relates to a cotton plant, or a part thereof, produced by this method.

In another embodiment, the present disclosure relates to a cotton plant produced by growing a seed of the cotton variety designated PX339054W3FE, or a part thereof, further comprising one or more transgenes. In a further aspect, the disclosure relates to a seed of this plant. In a further aspect, the disclosure relates to this cotton plant, wherein the one or more transgenes comprise a gene conferring upon said cotton plant insect resistance, disease resistance or virus resistance. In a further aspect, the disclosure relates to this cotton plant, wherein the gene conferring upon the cotton plant insect resistance is a *Bacillus thuringiensis* gene.

In another embodiment, the present disclosure relates to a cotton plant produced by growing a seed of the cotton variety designated PX339054W3FE, or a part thereof, wherein the plant or a parts thereof has been transformed so that its genetic material contains one or more transgenes operably linked to one or more regulatory elements. In a further aspect, the disclosure relates to this cotton plant, wherein the one or more transgenes comprise a gene conferring upon the cotton plant tolerance to an herbicide. In a further aspect, the disclosure relates to this cotton plant, wherein the herbicide is glyphosate, glufosinate, a phenoxy, a sulfonylurea or an imidazolinone herbicide, a hydroxyphenylpyruvate dioxygenase inhibitor or a protoporphyrinogen oxidase inhibitor.

In another embodiment, the present disclosure relates to a method for producing a population of PX339054W3FE progeny cotton plants comprising: (a) obtaining a first generation progeny cotton seed from a plant produced by growing a seed of the cotton variety designated PX339054W3FE as a parent; (b) growing the first generation progeny cotton seed to produce $F_1$ generation cotton plants and obtaining self or sib pollinated seed from the $F_1$ generation cotton plants; and (c) producing successive filial generations to obtain a population of PX339054W3FE progeny cotton plants. In a further aspect, the disclosure relates to the population of PX339054W3FE progeny cotton plants produced by this method, the population, on average, deriving 50% of its alleles from PX339054W3FE.

In another embodiment, the present disclosure relates to lint having substantially the same characteristics of the lint produced by cotton variety designated PX339054W3FE, representative seed of the variety having been deposited under ATCC Accession No. PTA-123652.

DETAILED DESCRIPTION OF THE INVENTION

I. Definitions of Plant Characteristics

In the description and examples that follow, a number of terms are used. To provide a clear and consistent understanding of the specification and claims, including the scope to be given such terms, the following definitions are provided.

*Alternaria macrospora*: This represents a visual assessment of the cotton plants for resistance to *Alternaria* leaf spot (*Alternaria macrospora*) rated as 0=not tested, 1=susceptible, or 2=moderately susceptible, 3=moderately resistant, or 4=resistant. causes *Alternaria* leaf spot Anthracnose: This represents a visual assessment of the cotton plants for resistance to Anthrancnose (*Colletotrichum* spp.) rated as 0=not tested, 1=susceptible, or 2=moderately susceptible, 3=moderately resistant, or 4=resistant.

Area(s) of Adaptation: This represents whether the cotton plant is adapted (A), not adapted (NA) or not tested (NT) for the following areas: Eastern, Delta, Central, Blacklands, Plains, Western, Arizona, and San Joaquin Valley.

*Ascochyta* Blight: This represents a visual assessment of the cotton plants for resistance to *Ascochyta* blight (*Ascochyta gossypii*) rated as 0=not tested, 1=susceptible, or 2=moderately susceptible, 3=moderately resistant, or 4=resistant.

Bacterial Blight (Race 1): This represents a visual assessment of the cotton plants for resistance to bacterial blight (race 1) (*Xanthomonas malvacearum*) rated as 0=not tested, 1=susceptible, or 2=moderately susceptible, 3=moderately resistant, or 4=resistant.

Bacterial Blight (Race 2): This represents a visual assessment of the cotton plants for resistance to bacterial blight (race 2) (*Xanthomonas malvacearum*) rated as 0=not tested, 1=susceptible, or 2=moderately susceptible, 3=moderately resistant, or 4=resistant.

Boll Breadth: This represents a comparison of the boll width at its middle and its base rated as broadest at base, or broadest at middle.

Boll Shape: This represents the shape of the boll rated as length less than width, length equal to width, or length more than width.

Boll Type: This represents the boll type rated as stormproof, storm resistant, or open.

Boll Weevil: This represents a visual assessment of the cotton plants for resistance to Boll Weevil (*Anthonomous grandis*) rated as 0=not tested, 1=susceptible, or 2=moderately susceptible, 3=moderately resistant, or 4=resistant.

Bollworm: This represents a visual assessment of the cotton plants for resistance to Bollworm (*Helicoverpa zea*) rated as 0=not tested, 1=susceptible, or 2=moderately susceptible, 3=moderately resistant, or 4=resistant.

Calyx Lobe: This represents the gossypol gland density on the calyx lobe rated as absent (normal), sparse, or more than normal.

Cotton Aphid: This represents a visual assessment of the cotton plants for resistance to Cotton Aphid (*Aphis gossypii*) rated as 0=not tested, 1=susceptible, or 2=moderately susceptible, 3=moderately resistant, or 4=resistant.

Cotton Fleahopper: This represents a visual assessment of the cotton plants for resistance to Cotton Fleahopper (*Pseudatomoscellis seriatus*) rated as 0=not tested, 1=susceptible, or 2=moderately susceptible, 3=moderately resistant, or 4=resistant.

Cotton Leafworm: This represents a visual assessment of the cotton plants for resistance to Cotton Leafworm (*Alabama argillacea*) rated as 0=not tested, 1=susceptible, or 2=moderately susceptible, 3=moderately resistant, or 4=resistant.

Cutworm: This represents a visual assessment of the cotton plants for resistance to Cutworm (*Agrotis ipsilon*) rated as 0=not tested, 1=susceptible, or 2=moderately susceptible, 3=moderately resistant, or 4=resistant.

Days to 75% Open Bolls: This represents the number of days from planting until which 75% of the bolls of a plant are open.

*Diplodia* Boll Rot: This represents a visual assessment of the cotton plants for resistance to *Diplodia* boll rot (*Diplodia gossypina*) rated as 0=not tested, 1=susceptible, or 2=moderately susceptible, 3=moderately resistant, or 4=resistant.

Distance to 1st Fruiting Branch: This represents the distance from the cotyledonary node to the first fruiting branch in centimeters.

Fall Armyworm: This represents a visual assessment of the cotton plants for resistance to Fall Armyworm (*Spodoptera frugiperda*) rated as 0=not tested, 1=susceptible, or 2=moderately susceptible, 3=moderately resistant, or 4=resistant.

Fiber Elongation: This represents the amount that a fiber sample will stretch before breakage and is a measure of the deformation of the cotton fiber at rupture expressed as percent change in length based on the original fiber length as measured by HVI.

Fiber Fineness: This represents a relative measure of size, diameter, linear density or weight per unit length expressed in terms of millitex or milligrams per tex unit.

Fiber Length: This represents fiber length expressed in hundredths of an inch as measured by High Volume Instrumentation (HVI).

Fiber Micronaire: This represents a measure of the fineness of the fiber. Within a cotton cultivar, micronaire is also a measure of maturity. Micronaire differences are governed by changes in perimeter or in cell wall thickness, or by changes in both. Within a variety, cotton perimeter is fairly constant and maturity will cause a change in micronaire. Consequently, micronaire has a high correlation with maturity within a variety of cotton. Maturity is the degree of development of cell wall thickness. Micronaire often does not have a good correlation with maturity between varieties of cotton having different fiber perimeter. Micronaire values range from about 2.0 to 6.0 and have the following meanings: below 2.9 very fine possible small perimeter but mature (good fiber), or large perimeter but immature (bad fiber); from 2.9 to 3.7 fine various degrees of maturity and/or perimeter; 3.8 to 4.6 average degree of maturity and/or perimeter; 4.7 to 5.5 coarse usually fully developed (mature), but larger perimeter; and 5.6 or greater very coarse fully developed, large-perimeter fiber.

Fiber Strength: This represents the force required to rupture or to break a bundle of fibers as measured in grams per tex on the HVI.

Fiber Uniformity: This represents the uniformity of fiber length in a sample as measured on the HVI, expressed as a percentage.

Fiber Yarn Tenacity: This represents the strength of a single strand of yarn; the force required to break a yarn.

Foliage: This represents the general appearance of the plant leaves rated as sparse, intermediate, or dense.

Fruiting Branch: This represents fruiting pattern rated as clustered, short, or normal.

*Fusarium* Wilt: This represents a visual assessment of the cotton plants for resistance to *Fusarium* Wilt (*Fusarium oxysporum*) rated as 0=not tested, 1=susceptible, or 2=moderately susceptible, 3=moderately resistant, or 4=resistant.

Gin Turnout: This represents the fraction of lint in a machine harvested sample of seed cotton (lint, seed, and trash).

Glyphosate Herbicide Resistance: Resistance of a plant to the action of glyphosate; conferred in crops by genetic transformation of the crop plant using a 5-enolpyruvylshikimate-3-phosphate synthase (EPSPS) gene that is insensitive to the effect of glyphosate, or a bacterial glyphosate oxidoreductase (GOX) gene that cleaves the nitrogen-carbon bond in glyphosate yielding aminomethylphosphonic acid.

Growth: This represents the growing pattern of the cotton plant following a fruiting cycle rated as determinate, i.e., a complete interruption of growth following a fruiting cycle, or indeterminate, i.e., a growth pattern in which stems continue to grow indefinitely.

Herbicide Resistance: When a plant has negligible effect from contact with an herbicide because the plant does not take up the herbicide or sequesters the herbicide in a manner that renders it essentially harmless.

Insect Resistance: When a plant has negligible effect from contact with a potentially harmful insect because the plant has a biochemical composition that repels, kills, or otherwise renders the insect essentially harmless to the plant.

Leaf Color: This represents a visual assessment of the leaf color of the cotton plant rated as greenish yellow, light green, medium green, dark green.

Leaf Glands: This represents the density of gossypol glands rated as absent, sparse, normal, or more than normal.

Leaf Nectaries: This represents whether leaf nectaries are present or absent on the uppermost fully expanded leaf.

Leaf Pubescence: This represents the density of leaf trichomes ("hairs") on the bottom surface excluding veins of the uppermost fully expanded leaf rated as absent, sparse, medium, or dense in terms of trichomes/cm$^2$.

Leaf Type: This represents the shape of the uppermost fully expanded leaf rated as normal, sub okra, okra, or super okra.

Lint Index: This represents the weight of lint per 100 seeds in grams.

Lint Percentage: This represents the lint (fiber) fraction of seed cotton (lint and seed).

Lint Yield: This represents the lint yield in pounds per acre.

*Lygus*: This represents a visual assessment of the cotton plants for resistance to *Lygus* (*Lygus hesperus*) rated as 0=not tested, 1=susceptible, or 2=moderately susceptible, 3=moderately resistant, or 4=resistant.

Mature Plant Height: This represents the height in centimeters of the cotton plant from the cotyledonary node to terminal.

Maturity (% Open Bolls): This represents the number of open bolls of a plant expressed as a percentage, generally measured about 2 weeks before 100% of the bolls of a plant are open Nodes to 1st Fruiting Branch: This represents the number of nodes from the cotyledonary node to the first fruiting branch, excluding the cotyledonary node.

Open Bolls: This represents the percentage of the bolls of a plant that are open at harvest.

Petal Color: This represents a visual assessment of the petal color rated as cream or yellow.

Petal Spot: This represents whether petal spot is present or absent on the flowers of the cotton plant.

*Phymatrotrichum* Root Rot: This represents a visual assessment of the cotton plants for resistance to *Phymatrotrichum* root rot (*Phymatrotrichum omnivore*) rated as 0=not tested, 1=susceptible, or 2=moderately susceptible, 3=moderately resistant, or 4=resistant.

Pink Bollworm: This represents a visual assessment of the cotton plants for resistance to Pink Bollworm (*Pectinophora gossypiella*) rated as 0=not tested, 1=susceptible, or 2=moderately susceptible, 3=moderately resistant, or 4=resistant.

Plant Habit: This represents the general growth habit of the plant rated as spreading, intermediate or compact.

Pollen Color: This represents a visual assessment of pollen color rated as cream or yellow.

*Pythium*: This represents a visual assessment of the cotton plants for resistance to *Pythium* (*Pythium* spp.) rated as 0=not tested, 1=susceptible, or 2=moderately susceptible, 3=moderately resistant, or 4=resistant.

Reniform Nematode: This represents a visual assessment of the cotton plants for resistance to Reniform Nematode (*Rotylenchulus reniformis*) rated as 0=not tested, 1=susceptible, or 2=moderately susceptible, 3=moderately resistant, or 4=resistant.

*Rhizoctonia solani*: This represents a visual assessment of the cotton plants for resistance to boll rot (*Rhizoctonia solani*) rated as 0=not tested, 1=susceptible, or 2=moderately susceptible, 3=moderately resistant, or 4=resistant.

Root-Knot Nematode: This represents a visual assessment of the cotton plants for resistance to Root-Knot Nematode (*Meloidogyne incognita*) rated as 0=not tested, 1=susceptible, or 2=moderately susceptible, 3=moderately resistant, or 4=resistant.

Seed-Cotton Weight Per Boll: This represents the average number of grams of seed cotton per boll on the cotton plant.

Seed Index: This represents the weight of 100 seeds in grams on a fuzzy basis.

Seeds Per Boll (Number): This represents the average number of seeds per boll on the cotton plant.

Southwestern Cotton Rust: This represents a visual assessment of the cotton plants for resistance to Southwestern Cotton Rust (*Puccinia cacabata*) rated as 0=not tested, 1=susceptible, or 2=moderately susceptible, 3=moderately resistant, or 4=resistant.

Spider Mite: This represents a visual assessment of the cotton plants for resistance to Spider Mite (*Tetranychus* spp.) rated as 0=not tested, 1=susceptible, or 2=moderately susceptible, 3=moderately resistant, or 4=resistant.

Stem Glands: This represents the density of gossypol glands rated as absent, sparse, normal, or more than normal.

Stem Lodging: This represents the general appearance of the plant stems relative to their normal near vertical orientation rated as lodging, intermediate, or erect.

Stem Pubescence: This represents whether the stem pubescence is glabrous, intermediate, or hairy.

Stink Bug: This represents a visual assessment of the cotton plants for resistance to Stink Bug (*Pitedia* spp.; *Euschistus* spp.; *Thyanta* spp.) rated as 0=not tested, 1=susceptible, or 2=moderately susceptible, 3=moderately resistant, or 4=resistant.

*Thielaviopsis basicola*: This represents a visual assessment of the cotton plants for resistance to black root rot (*Thielaviopsis basicola*) rated as 0=not tested, 1=susceptible, or 2=moderately susceptible, 3=moderately resistant, or 4=resistant.

Thrips: This represents a visual assessment of the cotton plants for resistance to Thrips (*Thrips* spp.) rated as 0=not tested, 1=susceptible, or 2=moderately susceptible, 3=moderately resistant, or 4=resistant.

Tobacco Bud Worm: This represents a visual assessment of the cotton plants for resistance to Tobacco Budworm (*Heliothis virescens*) rated as 0=not tested, 1=susceptible, or 2=moderately susceptible, 3=moderately resistant, or 4=resistant.

*Verticillium* Wilt: This represents a visual assessment of the cotton plants for resistance to (*Verticillium dahliae*) rated as 0=not tested, 1=susceptible, or 2=moderately susceptible, 3=moderately resistant, or 4=resistant.

II. Cotton Variety PX339054W3FE

A. Cotton Plant PX339054W3FE

In accordance with one aspect of the present disclosure, provided is a new Upland (*Gossypium hirsutum*) cotton seed and plants thereof designated PX339054W3FE. Further embodiments relate to a method for producing cotton seeds that includes, but is not limited to, the steps of planting seed of cotton variety PX339054W3FE in proximity to itself or to different seed from a same family or line, growing the resulting cotton plants under self-pollinating or sib-pollinating conditions with adequate isolation, and harvesting resultant seed obtained from such plants using techniques standard in the agricultural arts that are useful to bulk-up seed such as for hybrid production. Embodiments of the present disclosure also relate to varietal seed produced by such a method.

In any cross between cotton plant variety PX339054W3FE and another cotton plant variety, PX339054W3FE can be designated as the male (pollen parent) or the female (seed parent). Optionally, the seed of cotton variety PX339054W3FE can be pre-treated to increase resistance of the seed and/or seedlings to stressed conditions, and further, the cotton plants or surrounding soil can be treated with one or more agricultural chemicals before harvest. Such agricultural chemicals can include herbicides, insecticides, pesticides and the like. Embodiments of the present disclosure also relate to a cotton plant that expresses substantially all of the physiological and morphological characteristics of cotton plant variety PX339054W3FE and to a substantially homogenous population of cotton plants having all the physiological and morphological characteristics of cotton plant variety PX339054W3FE. Any cotton plants produced from cotton plant variety PX339054W3FE are contemplated in embodiments of the present disclosure and are, therefore, within the scope thereof. A description of physiological and morphological characteristics of cotton plant PX339054W3FE is presented in Table 1.

TABLE 1

Physiological and Morphological Characteristics of Cultivar PX339054W3FE

| Characteristic | Value[a] |
|---|---|
| Area(s) of Adaptation | Delta, Eastern, High Plains |
| Plant Habit | Intermediate |
| Foliage | Intermediate |
| Stem Lodging | Intermediate |
| Fruiting Branch | Normal |
| Growth | Indeterminate |
| Leaf Color | Medium green |
| Boll Shape | Length greater than width |
| Boll Breadth | Broadest at middle |
| % Open Bolls | 83.3 |
| Distance to 1st Fruiting Branch (cm) | 24.7 |
| Nodes to 1st Fruiting Branch (number) | 6.2 |
| Mature Plant Height (cm) | 101.5 |
| Leaf Type | Normal |
| Leaf Pubescence | Intermediate |
| Leaf Nectaries | Present |
| Stem Pubescence | Intermediate |
| Leaf Glands | Normal |
| Stem Glands | Normal |

TABLE 1-continued

Physiological and Morphological Characteristics of Cultivar PX339054W3FE

| Characteristic | Value[a] |
|---|---|
| Calyx Lobe | Absent |
| Petal Color | Cream |
| Pollen Color | Cream |
| Petal Spot | Absent |
| Seed Index (weight of 100 seeds in grams) | 8.9 |
| Lint Index (weight of 100 seeds in grams) | 7 |
| Lint Percentage | 43.8 |
| Seeds Per Boll (number) | 28.3 |
| Seed-Cotton Weight Per Boll (grams) | 4.8 |
| Boll Type | Open |
| Fiber Length (hundredths of an inch) | 1.17 |
| Fiber Uniformity (percentage) | 86.3 |
| Fiber Strength (grams per tex) | 35.6 |
| Fiber Elongation (percentage change) | 7.4 |
| Fiber Micronaire | 4.5 (4.3 to 5.3) |
| DISEASE AND INSECTS (0 = Not Tested, 1 = Susceptible, 2 = Moderately Susceptible, 3 = Moderately Resistant, 4 = Resistant) | |
| Bacterial Blight (Race 1) | 4 |
| TRANSGENES | |
| Insect Resistance | Bt Cry 1F, Bt Cry 1Ac, Vip3A |
| Herbicide Resistance | Glyphosate (MON 88913 event), 2,4-D, Glufosinate |

[a]These are typical values, which may vary due to the environment. Other values that are substantially equivalent are within the scope of this invention.

It will be appreciated by one having ordinary skill in the art that the values presented for the quantitative characteristics identified in Table 1 are typical values. These values can vary due to the environment and accordingly, other values that are substantially equivalent are also within the scope of embodiments of the disclosure.

Cotton variety PX339054W3FE shows uniformity and stability within the limits of environmental influence for the traits described in Table 1. Variety PX339054W3FE has been self-pollinated for a sufficient number of generations with careful attention paid to uniformity of plant type to ensure the homozygosity and phenotypic stability necessary to use in large scale, commercial production. The line has been increased both by hand and sib-pollination in isolated fields with continued observations for uniformity. No variant traits have been observed or are expected in PX339054W3FE.

Embodiments of the present disclosure also relate to one or more cotton plant parts of cotton plant PX339054W3FE. Cotton plant parts include plant cells, plant protoplasts, plant cell tissue cultures from which cotton plants can be regenerated, plant DNA, plant calli, plant clumps, and plant cells that are intact in plants or parts of plants, such as embryos, ovules, pollen, stigmas, flowers, petals, seeds, bolls, gossypol glands, stems, leaves, fibers, roots, root tips, and the like.

B. Cotton Seed Designated PX339054W3FE

A cotton seed is composed of three structural parts: (1) the pericarp, which is a protective outer covering (also known as bran or hull); (2) the germ (also known as an embryo); and (3) the endosperm. Another aspect of the present disclosure relates to one or more parts of cotton seed PX339054W3FE, such as the pericarp of cotton seed PX339054W3FE or the germ and/or the endosperm of cotton seed PX339054W3FE, which remain upon removal of the pericarp and adhering remnants of the seed coat.

Cotton seed designated PX339054W3FE can be provided as a substantially homogenous composition of cotton seed designated PX339054W3FE, that is, a composition that consists essentially of cotton seed PX339054W3FE. Such a substantially homogenous composition of cotton seed PX339054W3FE is substantially free from significant numbers of other varietal and/or hybrid seed so that the varietal seed forms from about 90% to about 100% of the total seed. Preferably, a substantially homogenous composition of the varietal cotton seed contains from about 98.5%, 99%, or 99.5% to about 100% of the varietal seed, as measured by seed grow outs. The substantially homogenous composition of varietal cotton seed of embodiments of the disclosure can be separately grown to provide substantially homogenous populations of varietal cotton plants. However, even if a population of varietal cotton plants is present in a field with other different cotton plants, such as in a commercial seed-production field of single-cross hybrid cotton planted in a ratio of 1 male pollinator row to 4 female seed-parent rows, such a population will still be considered to be within the scope of embodiments of the present disclosure.

Cotton yield is affected by the conditions to which seeds and seedlings (young plants grown from seeds) are exposed. Seeds and seedlings can be exposed to one of, or a combination of, for example, cold, drought, salt, heat, pollutants, and disease, all of which are conditions that potentially retard or prevent the growth of crops therefrom. For example, temperature extremes are typical in the United States. Furthermore, diseases evolved from pathogens and deterioration caused by fungi are potentially harmful to seeds and seedlings. Thus, it is desirable to treat seeds by, for example, coating or impregnating the seeds with compositions that render the seeds and seedlings grown therefrom more hardy when exposed to such adverse conditions.

Accordingly, another aspect of the present disclosure relates to a coated and/or impregnated seed or cotton variety designated PX339054W3FE and to coated and/or impregnated seed derived therefrom. Various agents have been used to treat seeds to increase resistance of the plants to stressed conditions, such as cold, drought, salt, and fungi. Such agents include, for example, sodium methylphenyl-pentadienoate, trichloroacetic acid, polyoxyalkylene-organo-siloxane block copolymer, 5-aminolevulinic acid, salicylic acid, thiamethoxam, potassium chloride, and polyvinyl alcohol and are useful alone, or in combination in embodiments of the present disclosure.

When pre-treating seeds in accordance with embodiments of the present disclosure, such as before the seeds are planted, the seeds are contacted with the composition of interest, for example by coating seeds, spraying seeds, soaking seeds, or a combination thereof, by methods well known to those skilled in the art.

C. Deposit Information

Applicants have made a deposit of at least 2,500 seeds of cotton variety PX339054W3FE with the American Type Culture Collection (ATCC), Manassas, Va. 20110 USA, under ATCC Accession No. PTA-123652. The seeds deposited with the ATCC on Nov. 15, 2016 were taken from a repository maintained by Phytogen Seed Company since before the filing date of this application. Access to the ATCC deposit will be available during the pendency of the application to the Commissioner of Patents and Trademarks and persons determined by the Commissioner to be entitled thereto upon request. Upon allowance of any claims in the application, the Applicant(s) will maintain and will make this deposit available to the public pursuant to the Budapest Treaty.

III. Processes of Preparing Novel Cotton Plants

A. Novel Cotton Plants Obtained from Variety PX339054W3FE

Various breeding schemes can be used to produce new cotton varieties from cotton variety PX339054W3FE. In one method, generally referred to as the pedigree method, PX339054W3FE can be crossed with another different cotton plant such as a second parent cotton plant variety, which either itself exhibits one or more selected desirable characteristic(s) or imparts selected desirable characteristic(s) to a hybrid combination. Examples of potentially desired characteristics include greater yield, better stalks, better roots, reduced time to crop maturity, better fiber quality (e.g. fineness, length, length uniformity, strength, reflectance), better storm resistance, better agronomic quality, higher nutritional value, higher starch extractability or starch fermentability, resistance and/or tolerance to insecticides, herbicides, pests, heat and drought, and disease, and uniformity in germination times, stand establishment, growth rate, maturity and boll size. If the two original parent cotton plants do not provide all the desired characteristics, then other sources can be included in the breeding population. Elite varieties can also be used as starting materials for breeding or source populations from which to develop new varieties.

Thereafter, resulting seed is harvested and resulting superior progeny plants are selected and selfed or sib-mated in succeeding generations, such as for about 5 to about 7 or more generations, until a generation is produced that no longer segregates for substantially all factors for which the varietal parents differ, thereby providing a large number of distinct, pure-breeding varieties.

In another embodiment for generating new cotton varieties, generally referred to as backcrossing, one or more desired traits can be introduced into parent cotton plant variety PX339054W3FE (the recurrent parent) by crossing the PX339054W3FE plants with another cotton plant (referred to as the donor or non-recurrent parent), which carries the gene(s) encoding the particular trait(s) of interest to produce $F_1$ progeny plants. Both dominant and recessive alleles can be transferred by backcrossing. The donor plant can also be a varietal cotton plant, but in the broadest sense can be a member of any plant variety or population cross-fertile with the recurrent parent. Next, $F_1$ progeny plants that have the desired trait are selected. Then, the selected progeny plants are crossed with PX339054W3FE to produce backcross progeny plants. Thereafter, backcross progeny plants comprising the desired trait and the physiological and morphological characteristics of cotton variety PX339054W3FE are selected. This cycle is repeated for about one to about eight cycles, preferably for about 3 or more times in succession to produce selected higher backcross progeny plants that comprise the desired trait and all of the physiological and morphological characteristics of cotton variety PX339054W3FE listed in Table 1 as determined at the 5% significance level when grown in the same environmental conditions. Exemplary desired trait(s) include insect resistance, cytoplasmic male sterility, enhanced fiber quality, enhanced nutritional quality, herbicide resistance, yield stability, yield enhancement, storm resistance, drought tolerance, and resistance to bacterial, fungal, nematode and viral disease. One of ordinary skill in the art of plant breeding will appreciate that a breeder uses various methods to help determine which cotton plants will be selected from the segregating populations and ultimately which varieties will be used commercially and will be used to develop hybrids for commercialization. In addition to the knowledge of the germplasm and other skills the breeder uses, a part of the selection process is dependent on experimental design coupled with the use of statistical analysis.

Experimental design and statistical analysis are used to help determine which plants, which family of plants, and finally which varieties and hybrid combinations are significantly better or different for one or more traits of interest. Experimental design methods are used to assess error so that differences between two varieties or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding knows how to evaluate the traits of two plant varieties to determine if there is no significant difference between the two traits expressed by those varieties. For example, see Fehr, Walt, Principles of Cultivar Development, p. 261-286 (1987), which is incorporated herein by reference in its entirety. Mean trait values can be used to determine whether trait differences are significant, and preferably the traits are measured on plants grown under the same environmental conditions.

This method results in the generation of cotton plants with substantially all of the desired morphological and physiological characteristics of the recurrent parent and the particular transferred trait(s) of interest. Because such cotton plants are heterozygous for loci controlling the transferred trait(s) of interest, the last backcross generation is subsequently selfed to provide pure breeding progeny for the transferred trait(s).

Backcrossing can be accelerated by the use of genetic markers such as SSR, RFLP, SNP or AFLP markers to identify plants with the greatest genetic complement from the recurrent parent.

Direct selection can be applied where a single locus acts as a dominant trait, such as the herbicide resistance trait. For this selection process, the progeny of the initial cross are sprayed with the herbicide before the backcrossing. The spraying eliminates any plants that do not have the desired herbicide resistance characteristic, and only those plants that have the herbicide resistance gene are used in the subsequent backcross. In some embodiments where the characteristic being transferred is a recessive allele, it is advisable to introduce a test of the progeny to determine if the desired characteristic has been successfully transferred. The process of selection, whether direct or indirect, is then repeated for all additional backcross generations.

It will be appreciated by those having ordinary skill in the art that backcrossing can be combined with pedigree breeding, as where variety PX339054W3FE is crossed with another cotton plant, the resultant progeny are crossed back to variety PX339054W3FE and thereafter, the resulting progeny of this single backcross are subsequently inbred to develop new varieties. This combination of backcrossing and pedigree breeding is useful when recovery is desired of fewer than all of the PX339054W3FE characteristics that will be obtained by a conventional backcross.

In an additional embodiment of the present disclosure, new cotton varieties can be developed by a method generally referred to as haploid breeding. In this methodology, haploid plants are generated from diploid, heterozygous cotton plants that result from crossing cotton plant variety PX339054W3FE with another, different cotton plant. Such haploid cotton plants can be generated by methods known to those skilled in the art such as by culturing haploid anthers or embryos from a diploid plant. Alternately, such haploid cotton plant can be generated by crossing the diploid heterozygous cotton plant with a cotton plant that comprises a haploid inducing gene, which, when present in the female parent results in offspring with a greatly enhanced frequency of haploids of both maternal and paternal origin. Thereafter, homozygous diploid plants are produced by the doubling of a set of chromosomes (1N) from a haploid plant generated by self-pollination such as through use of a doubling agent, such as colchicine, nitrous oxide gas, heat treatment and trifluralin. The technique of haploid breeding is advantageous because no subsequent inbreeding is required to obtain a homozygous plant from a heterozygous source. Thus, in another aspect of this disclosure, a new cotton plant variety is developed by a method that includes the steps of crossing PX339054W3FE or a hybrid made with PX339054W3FE with another cotton plant having a propensity to generate haploids to produce haploid progeny plants, and selecting desirable cotton plants from the haploid progeny plants.

Embodiments of the present disclosure also relate to novel cotton plants produced by a method generally referred to as mutation breeding, whereby one or more new traits can be artificially introduced into cotton variety PX339054W3FE. The goal of artificial mutagenesis is to increase the rate of mutation for a desired characteristic. Mutation rates can be increased by use of many different factors, including: temperature; long-term seed storage; tissue culture conditions; radiation, such as X-rays, Gamma rays (e.g. Cobalt-60 or Cesium-137), neutrons, (product of nuclear fission by Uranium-235 in an atomic reactor), Beta radiation (emitted from radioisotopes such as Phosphorus-32 or Carbon-14), or ultraviolet radiation (preferably from 2500 to 2900 nm); or chemical mutagens, such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis and selected, the trait can then be incorporated into existing germplasm by traditional breeding techniques. Details of mutation breeding can be found in "Principles of Cultivar Development", Fehr, 1993 Macmillan Publishing Company, the disclosure of which is incorporated herein by reference in its entirety.

The mutagenesis treatment can be applied to various stages of plant development, including but not limited to cell cultures, embryos, microspores and shoot apices as well as to cotton seeds. By way of example, pollen can be mixed with a solution of 1 mL EMS and 100 mL Fisher paraffin oil (stock diluted by 1 mL and 15 mL oil solution) every minute for the first 5 minutes and then every five minutes for 45 minutes to keep the pollen suspended. Thereafter, the pollen/paraffin oil solution is brushed onto the stigmas of emasculated flower buds. A paper soda straw is used to cover the stigma to prevent contamination. The cotton boll is picked at maturity and then resultant seeds or the plants therefrom are screened for the desired mutant trait(s).

Once new varieties are created; the next step is to determine if the new varieties have any value. This is accomplished by techniques of measuring the combining ability of the new varietal plant, as well as the performance of the variety itself. Combining ability refers to a variety's contribution as a parent when crossed with other varieties to form hybrids. Specific combining ability (SCA) refers to the ability of a variety to cross to another specific variety to form a hybrid. General combining ability (GCA) refers to the ability of a variety to cross to a wide range of varieties to form hybrids. The methodology of forming hybrids to evaluate a variety's contribution as a parent for the purpose of selecting superior varieties is interchangeably known as experimental, top or test crossing.

B. Novel Varieties Obtained from a Hybrid Having Variety PX339054W3FE as a Parent In accordance with embodiments of the present disclosure, a hybrid plant having variety PX339054W3FE as a parent is crossed with itself or any different cotton plant such as a varietal cotton plant or a hybrid cotton plant to develop a novel variety. For example, a hybrid cotton plant having cotton plant variety PX339054W3FE as a parent can be inbred, i.e., crossed to itself or sib-pollinated, and the resulting progeny each selfed for about 5 to about 7 or more generations, thereby providing a set of distinct, relatively pure-breeding varieties wherein each of the varieties received all of its alleles from the hybrid cotton plant having cotton plant variety PX339054W3FE as a parent. Double haploid methods can also be used to obtain a cotton plant variety that is homozygous at essentially every locus, wherein the cotton plant variety received all of its alleles from the hybrid cotton plant having cotton plant PX339054W3FE as a parent. In other embodiments, a hybrid cotton plant having cotton plant variety PX339054W3FE as a parent is crossed with a different cotton plant, such as any varietal cotton plant that is not varietal cotton plant PX339054W3FE, any hybrid cotton plant that does not have PX339054W3FE as a parent, another germplasm source, a haploid or mutation inducing stock, or a trait donor plant, thereby providing a set of distinct, relatively pure-breeding varieties. The resulting varieties can then be crossed with other varieties or other cotton germplasm and the resulting progeny analyzed for beneficial characteristics. In this way, novel varieties conferring desirable characteristics can be identified.

C. "Chasing Selfs"

In the event that commercial cotton hybrids are developed, both female and male varietal seed is occasionally found within a commercial bag of hybrid seed. Chasing the selfs involves identifying parental varietal plants within a stand of cotton that has been grown from a bag of hybrid cotton seed. Once the seed is planted, the parental plants can be identified and selected due to their variance from the population norm, i.e., by their stature, fruiting branch structure, leaf shape, leaf pubescence, fiber quality traits, or yield components relative to the hybrid plants that grow from the hybrid seed that predominates in a commercial bag of hybrid seed. By locating the parental plants, isolating them from the rest of the plants, and self-pollinating them (i.e., "chasing selfs"), a breeder can obtain a variety that is identical to a parent used to produce the hybrid.

Accordingly, another embodiment of the present disclosure is directed to a method for producing cotton plant variety PX339054W3FE comprising: (a) planting a collection of seed, such as a collection of seed comprising seed of a hybrid, one of whose parents is cotton variety PX339054W3FE, the collection also comprising seed of the variety; (b) growing plants from said collection of seed; (c) identifying parent plants; (d) controlling pollination in a manner that preserves substantial homozygosity of the parent plant; and, (e) harvesting resultant seed. Step (c) can further comprise identifying plants with decreased vigor, i.e., plants that appear less robust than the other plants, or identifying plants that have a genetic profile in accordance with the genetic profile of PX339054W3FE. Cotton plants capable of expressing substantially all of the physiological and morphological characteristics of cotton variety PX339054W3FE include cotton plants obtained by chasing selfs from a bag of hybrid seed.

One having skill in the art will recognize that once a breeder has obtained cotton variety PX339054W3FE by chasing selfs from a bag of hybrid seed, the breeder can then produce new varietal plants such as by sib-pollinating, i.e., crossing the cotton plant PX339054W3FE with another cotton plant PX339054W3FE, or by crossing the cotton plant PX339054W3FE with a hybrid cotton plant obtained by growing the collection of seed.

IV. Novel Hybrid Plants

A. Novel Hybrid Seeds and Plants

In yet another aspect of the disclosure, processes are provided for producing cotton seeds or plants, which processes generally comprise crossing a first parent cotton plant with a second parent cotton plant, wherein at least one of the first parent cotton plant or the second parent cotton plant is parent cotton plant variety PX339054W3FE. In some embodiments of the present disclosure, the first cotton plant variety is PX339054W3FE and is a female and in other embodiments the first cotton plant variety is PX339054W3FE and is a male. These processes can be further exemplified as processes for preparing hybrid cotton seed or plants, wherein a first cotton plant variety is crossed with a second cotton plant of a different, distinct variety to provide a hybrid that has, as one of its parents, the cotton plant variety PX339054W3FE. In this case, a second variety is selected that confers desirable characteristics when in hybrid combination with the first variety. In these processes, crossing will result in the production of seed and lint. The seed and lint production occurs regardless whether the seed and/or lint are collected.

Any time the cotton plant variety PX339054W3FE is crossed with another, different cotton variety, a first generation ($F_1$) cotton hybrid plant is produced. As such, an $F_1$ hybrid cotton plant can be produced by crossing PX339054W3FE with any second cotton plant variety. Therefore, any $F_1$ hybrid cotton plant or cotton seed that is produced with PX339054W3FE as a parent is within the scope of embodiments of the present disclosure.

When cotton plant variety PX339054W3FE is crossed with another cotton plant variety to yield a hybrid, the original variety can serve as either the maternal or paternal plant with, basically, the same characteristics in the hybrids. Occasionally, maternally inherited characteristics can express differently depending on the decision of which parent to use as the female. However, often one of the parental plants is preferred as the maternal plant because of increased seed and/or lint yield and preferred production characteristics, such as optimal seed size and quality or ease of boll or lint removal. Particularly in very hot climates, such as in the Southwest USA, pollen can be shed better by one plant, making that plant the preferred male parent. It is generally preferable to use PX339054W3FE as the male parent.

In embodiments of the present disclosure, the first step of "crossing" the first and the second parent cotton plants comprises planting, preferably in pollinating proximity, seeds of a first cotton plant variety and a second, distinct cotton plant variety. As discussed herein, the seeds of the first cotton plant variety and/or the second cotton plant variety can be treated with compositions that render the seeds and seedlings grown therefrom more hardy when exposed to adverse conditions.

A further step comprises cultivating or growing the seeds of the first and second parent cotton plants into plants that bear flowers. If the parental plants differ in timing of sexual maturity, techniques can be employed to obtain an appropriate nick, i.e., to ensure the availability of pollen from the parent cotton plant designated the male during the time at which stigmas on the parent cotton plant designated the female are receptive to the pollen. Methods that can be employed to obtain the desired nick include delaying the flowering of the faster maturing plant, such as, but not limited to, delaying the planting of the faster maturing seed, cutting or burning the top leaves of the faster maturing plant (without killing the plant) or speeding up the flowering of the slower maturing plant, such as by covering the slower maturing plant with film designed to speed germination and growth.

In a preferred embodiment, the cotton plants are treated with one or more agricultural chemicals as considered appropriate by the grower.

A subsequent step comprises preventing self-pollination or sib-pollination of the plants, i.e., preventing the stigmas of a plant from being fertilized by any plant of the same variety, including the same plant. This is preferably done in large scale production by controlling the male fertility, e.g., treating the flowers so as to prevent pollen production or alternatively, using as the female parent a male sterile plant of the first or second parent cotton plant (i.e., treating or manipulating the flowers so as to prevent pollen production, to produce an emasculated parent cotton plant, or using as a female a cytoplasmic male sterile version of the cotton plant). This control can also be accomplished in small scale production by physical removal of the staminal column of individual flowers before anthesis to provide effective control of unwanted self-pollination or sib-pollination.

Yet another step comprises allowing cross-pollination to occur between the first and second parent cotton plants. When the plants are not in pollinating proximity, this is done by either collecting ripe, undehisced anthers from a flower on the pollen parent with a short section of a soda straw during the same evening of the emasculations, or collecting whole, freshly dehisced flowers during the next morning after the emasculations. The soda straw containing the ripe anthers is then slipped over the stigma of an emasculated flower. Finally, bracts are wired around the soda straw, holding it in place over the style, thus protecting the stigma from foreign pollen. If a whole flower from the male parent is used, the petals are folded down and the staminal column is rubbed onto the emasculated stigma. In small-scale production, seeds of hybrid cotton are commercially produced by hand emasculation and pollination, or by hand pollination of genetic male-sterile cotton. In large scale production, seed of hybrid cotton are commercially produced by using various bees and other insect pollinators to cross pollinate genetic or cytoplasmic male-sterile cotton, or cotton that has been treated with a chemical that results in male sterility.

A further process comprises harvesting the seeds and/or lint, near or at maturity, from the bolls of the plants that received the pollen. In a particular embodiment, seed and/or lint are harvested from the female parent plant, and when desired, the harvested seed can be grown to produce a first generation ($F_1$) hybrid cotton plant.

Yet another process comprises ginning the seed cotton to separate the seed from the marketable lint and delinting the "fuzzy" seed to remove the short "linters" that remain attached after ginning. The seeds are further conditioned and treated with chemicals such as fungicides and insecticides prior to being packaged for sale to growers for the production of lint and seed. As with varietal seed, in some embodiments it is desirable to treat hybrid seeds with compositions that render the seeds and seedlings grown therefrom more hardy when exposed to adverse conditions. The resulting hybrid seed is sold to growers for the production of seed and lint and not generally for breeding.

Further embodiments of the present disclosure relate to a hybrid cotton plant produced by growing the harvested seeds produced on the male-sterile plant, as well as seed produced by the hybrid cotton plant.

A single cross hybrid is produced when two different parent cotton plant varieties are crossed to produce first generation $F_1$ hybrid progeny. Generally, each parent cotton plant variety has a genotype that complements the genotype of the other parent variety. Typically, the $F_1$ progeny are more vigorous than the respective parent cotton plant varieties. This hybrid vigor, or heterosis, is manifested in many polygenic traits, including markedly improved yields and improved fruiting, roots, uniformity and insect and disease resistance. It is for this reason that single cross $F_1$ hybrids are generally the most sought-after hybrid. A three-way, or modified single-cross hybrid is produced from three varieties where two of the varieties are crossed (A×B) and then the resulting $F_1$ hybrid is crossed with the third variety (A×B)× C, as where a modified female is used in the cross. A modified female provides an advantage of improved seed/lint parent yield whereas a modified male improves pollen flow. A double cross hybrid is produced from four varieties crossed in pairs (A×B and C×D), thereby resulting in two $F_1$ hybrids that are crossed again. Double cross hybrids are more common in countries wherein less demand exists for higher yielding single cross hybrids. Synthetic populations or crosses are developed by crossing two or more varieties (or hybrids, or germplasm sources) together and then employing one of many possible techniques to random mate the progeny. Random mating the progeny is any process used by plant breeders to make a series of crosses that will create a new germplasm pool from which new breeding germplasm can be derived. Since cross pollination of male sterile cotton plants by hand or by various insects is generally very inefficient, $F_1$ hybrid seed is generally too expensive to produce on a large scale. Consequently, in some embodiments the $F_2$ seed harvested from $F_1$ hybrids retains suitable heterosis to be an economically viable option to pure-line varieties.

The utility of the cotton plant variety PX339054W3FE also extends to crosses with species other than the *hirsutum* species, such as *barbadense*. Commonly, suitable species will be of the family Malvaceae, and especially of the genera *Gossypium*.

B. Cotton Varietal Comparison

As mentioned above, experimental strains are progressively eliminated following detailed evaluations of their phenotype, including formal comparisons with other commercially successful varieties. Research small-plot trials and commercial strip trials are used to compare the phenotypes of varieties grown in as many environments as possible. They are performed in many environments to assess overall performance of the new varieties and to select optimum growing conditions. Because the cotton strains and varieties are grown in close proximity, differential effects of environmental factors that affect gene expression, such as moisture, temperature, sunlight, and pests, are minimized. For a decision to be made to advance a strain, it is not necessary that the strain be better than all other varieties. Rather, significant improvements must be shown in at least some traits that will create value for some applications or markets. Some experimental strains are eliminated, despite being similarly competitive relative to the current commercial varieties, because the cost to bring a new variety to market requires a new product to be a significant improvement over the existing product offering. Such varieties can also be licensed to other parties who have a need in their commercial product portfolio.

PX339054W3FE was evaluated for lint yield at 4 locations with 4 replications per location in 2015. The test locations were near Fairhope, Ala.; Bainbridge, Ga.; Leland, Miss.; and Suffolk, Va. PX339054W3FE had similar lint yield compared to DP1522B2XF, PHY333WRF, PHY490W3FE, PHY499WRF and PHY552WRF over all locations (Table 2). The maturity of PX339054W3FE was similar to the mid-maturing varieties of DP1522B2XF, PHY333WRF, PHY490W3FE, PHY499WRF and PHY552WRF.

TABLE 2

Comparison of Lint Yield and Open Bolls[a] Between PX339054W3FE and Similarly Adapted Cotton Cultivars

| Cultivar | Lint Yield (lbs/acre)[b] | Open Bolls (%)[c] |
| --- | --- | --- |
| DP1522B2XF | 1581 b | 83.3 a |
| PHY333WRF | 1625 ab | 86.7 a |
| PHY490W3FE | 1533 b | 73.3 a |
| PHY499WRF | 1797 a | 76.7 a |
| PHY552WRF | 1585 ab | 76.7 a |
| PX339054W3FE | 1617 ab | 83.3 a |

Means followed by the same letter do not significantly differ; calculated with Tukey's W procedure at 95%.
[a]Higher percentage open bolls indicates earlier maturity at harvest.
[b]Means across 4 environments.
[c]Data from 1 environment.

PX339054W3FE appears stable and uniform in isolated field seed production and field-trial evaluations, and no off-type plants have been exhibited. This line has exhibited commercial value in field evaluations and is well adapted to the High Plains, the Mississippi Delta and the Southeastern United States production regions where mid-maturity varieties are grown. It will be of value to cotton producers who desire a cotton variety that has insect resistance from Bt genes in addition to herbicide resistance.

V. Novel PX339054W3FE-Derived Plants

All plants produced using cotton plant variety PX339054W3FE as a parent are within the scope of embodiments of this disclosure, including plants derived from cotton plant variety PX339054W3FE. This includes plants essentially derived from variety PX339054W3FE, where the term "essentially derived variety" has the meaning ascribed to such term in 7 U.S.C. § 2104(a)(3), also known as Section 2104(a)(3) of the Plant Variety Protection Act, which section is hereby incorporated by reference in its entirety. This also includes a progeny plant and parts thereof with at least one ancestor that is cotton plant variety PX339054W3FE, and more specifically, where the pedigree of this progeny includes 1, 2, 3, 4, and/or 5 or cross pollinations to cotton plant PX339054W3FE, or a plant that has PX339054W3FE as a progenitor. All breeders of ordinary skill in the art maintain pedigree records of their breeding programs. These pedigree records contain a detailed description of the breeding process, including a listing of all parental lines used in the breeding process and information on how such line was used. Thus, a breeder will know if PX339054W3FE were used in the development of a progeny line, and will also know how many breeding crosses to a line other than PX339054W3FE were made in the development of any progeny line. A progeny line so developed can then be used in crosses with other, different, cotton varieties to produce first generation F1 cotton hybrid seeds and plants with superior characteristics.

Accordingly, another aspect of the present disclosure relates to methods for producing a PX339054W3FE-derived cotton plant. Embodiments of such methods for producing a PX339054W3FE-derived cotton plant comprise: (a) crossing cotton plant PX339054W3FE with a second cotton plant to yield progeny cotton seed; and (b) growing the progeny cotton seed (under plant growth conditions) to yield the PX339054W3FE-derived cotton plant. Such methods can further comprise the steps of: (c) crossing the PX339054W3FE-derived cotton plant with itself or another cotton plant to yield additional PX339054W3FE-derived progeny cotton seed; (d) growing the progeny cotton seed of step (b) (under plant growing conditions) to yield additional PX339054W3FE-derived cotton plants; and (e) repeating the crossing and growing steps of (c) and (d) from 0 to 7 times to generate further PX339054W3FE-derived cotton plants. Still further, this can comprise utilizing methods of semigamy and other haploid breeding and plant tissue culture methods to derive progeny of the PX339054W3FE-derived cotton plant.

VI. Tissue Cultures and In Vitro Regeneration of Cotton Plants

As is well known in this art, tissue culture of cotton can be used for the in vitro regeneration of a cotton plant. Accordingly, further aspects of the disclosure relate to tissue cultures of the cotton plant variety designated PX339054W3FE, to tissue cultures of hybrid and derived cotton plants obtained from PX339054W3FE, to plants obtained from such tissue cultures and to the use of tissue culture methodology in plant breeding. The term "tissue culture" includes a composition comprising isolated cells of the same type, isolated cells of different types, or a collection of such cells organized into parts of a plant. Exemplary tissue cultures are protoplasts, calli and plant cells that are intact in plants or parts of plants, such as embryos, pollen, ovules, flowers, petals, seeds, bolls, gossypol glands, stems, leaves, fibers, roots, root tips, and the like. In a preferred embodiment, the tissue culture comprises embryos, protoplasts, meristematic cells, pollen, leaves or anthers derived from immature tissues of these plant parts.

A. Cotyledon Culture

To obtain plant tissue for callus culture initiation, seeds are harvested from a wild type cotton plant (generally GC510 or Coker310 genotype). Initially, seeds are surface sterilized by a triple rinse with 70% ethanol for 1 minute each, a thorough rinse with sterile water, followed by a wash in 30% commercial bleach (0.1% sodium hypochlorite) for about 20 minutes.

Seeds are rinsed in sterile distilled water, and seeds are placed on the surface of germination media (LS salts (10×), 3% sucrose, modified B5 vitamins (1000×), at pH 5.8) for the production of sterile plantlets. At approximately, 7-10 days post plating, plantlets will have emerged from the seeds. The "first true leaves" are the cotyledons. Generally, tissue culture media contains amino acids, salts, sugars, hormones, and vitamins. The proportion of one ingredient versus another depends on the application (e.g., need for rooting versus shoot elongation). At day 7-10, the cotyledons are of sufficient size for experimental use. The cotyledons are cut into 1 mm square pieces and plated on callus induction media (100 mL/L LS salts (10×), 3% glucose, 1 mL/L modified B5 vitamins (1000×), 1 ml/L 1 mM kinetin, 1 ml/L 1 mM 2,4-D, 8 g/L noble agar, pH 5.8). The cotyledon segment is placed on the media in the abaxial side down orientation. After three weeks on the callus induction media, callus forms around the cut edges of the segment; the callus is removed from the edges using a scalpel. The "callus" is a loose collection or mass of undifferentiated cells, which can be yellow-green in color. Some lines are prone to phenolic production (browning), which can affect growth. The callus is maintained on the initiation media for nine weeks, with subculture to fresh media every three weeks. If the segments undergo transformation, they are co-cultured with *Agrobacterium* in callus induction media for 3 days and then transferred to callus induction media supplemented with carbenicillin, which is an antibiotic to kill the *Agrobacterium* (2 ml/L), and glufosinate-ammonium (0.5 ml/L), which is the selective agent that allows growth of only those cells that contain a transgene (PAT).

At week nine, the callus is transferred to growth media (100 ml/L LS salts, 3% glucose, 1 ml/L B5 vitamins, 4.6 ml/L kinetin, 10.7 mL/L NAA, 8 g/L noble agar, pH 5.8, and, if *Agrobacterium* infection was used to transfer the PAT gene, carbenicillin (0.4 ml/L) and glufosinate ammonium (0.3 ml/L)). The callus will remain on this media for 3 weeks, to allow for increased growth before going to embryogenic callus induction media. Once sufficient callus is present, the tissue is placed on embryogenic induction media (1 pkg DKW salts, 10 ml/L myo-inositol, 1 ml/L B5 vitamins, 2% glucose, 8 g/L noble agar, pH 5.8). The time for a line to produce embryogenic callus varies from two to six months; during which time the callus remains on the same plate of media. Stress can assist in inducing cotton callus to become embryogenic.

Regeneration begins with embryogenic callus. Embryogenic callus is maintained on the embryogenic callus induction media, with two week subcultures to fresh media. Microscope use is preferred for the isolation and transfer of embryogenic callus to ensure the desired morphology is taken from the plates. The desired morphology has a granular appearance, yellow-green in color. The embryogenic callus will give rise to embryos, which can look like small footballs and have a green color. The embryos mature on the embryogenic callus induction media. It can take three to nine weeks for the embryos to mature or elongate; transfers are carried out at three-week intervals. At the mature or elongated stage the embryos are transferred to basal media that will improve shoot (1 pkg DKW salts, 10 mL/L myo-inositol, 1 mL/L modified B5 vitamins, 3% sucrose, 0.5 mL/L kinetin, 8 g/L noble agar, pH 5.8) or root development (0.5 pkg DKW salts, 5 mL/L myo-inositol, 0.5 mL/L modified B5 vitamins, 1% sucrose, 8 g/L noble agar, pH 5.8).

When secondary roots have formed and the shoot is 1 to 2 inches high with 2 good leaves, the cotton plant is ready for soil. Plantlets are first placed in a Conviron in small pots with a humidi-dome to assist with plant hardening, since cotton plants can be quite fragile. Then plants are later transferred to large pots in the greenhouse. Most cotton plants are allowed to self-pollinate and these flowers are tagged with one color, while others can be crossed with an elite variety and tagged separately.

B. Additional Tissue Cultures and Regeneration

Other methods for preparing and maintaining plant tissue cultures are well known in the art. By way of example, reference may be had to Komatsuda, T. et al., Crop Sci. 31:333-337 (1991); Stephens, P. A., et al., Theor. Appl. Genet. 82:633-635 (1991); Komatsuda, T. et al., Plant Cell, Tissue and Organ Culture, 28:103-113 (1992); Dhir, S. et al., Plant Cell Reports 11:285-289 (1992); Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this disclosure relates to cells that upon growth and differentiation produce cotton plants having the physiological and morphological characteristics of the present cotton variety.

VII. Male Sterility

Methods for controlling male fertility in cotton plants offer the opportunity for improved plant breeding, particularly for the development of cotton hybrids that require the implementation of a male sterility system to prevent the varietal parent plants from self-pollination.

Accordingly, another aspect of the present disclosure relates to male-sterile varietal cotton plants designated PX339054W3FE and the production of hybrid cotton seed using a male sterility system with such varietal female parent plants that are male sterile. If cotton variety PX339054W3FE is employed as the female parent, PX339054W3FE can be rendered male-sterile by, for example, removing the stamens of PX339054W3FE parental plants manually. By way of example, alternate strips of two cotton varieties can be planted in a field followed by manual emasculation. Provided that the female variety is sufficiently isolated from foreign cotton pollen sources, the stigma of the emasculated variety will be fertilized only from the other male variety either manually or by insect pollinator vectors, and the resulting seed will therefore be hybrid seed.

The laborious and occasionally unreliable manual emasculation process can be minimized by using cytoplasmic male-sterile (CMS) varieties. Plants of a CMS variety are male sterile as a result of the influence of cytoplasmic factors, rather than those of the nuclear genome. Thus, this characteristic is inherited exclusively through the female parent in cotton plants, since CMS plants are fertilized with pollen from another variety that is not male-sterile. In some embodiments, pollen from the second variety contributes genes that make the hybrid plants male-fertile. Seed from emasculated fertile cotton and CMS produced seed of the same hybrid can be blended to insure that adequate pollen loads are available for fertilization when the hybrid plants are grown. Conventional backcrossing methods can be used to introgress the CMS trait into variety PX339054W3FE.

Alternatively, haploid breeding methods can also be employed to convert variety PX339054W3FE to CMS sterility. Haploids are plants that contain only one-half of the chromosome number present in diploid somatic cells, which are cells other than haploid cells, such as those found in the germ. There are a few stocks or genetic systems in cotton that are known to generate haploids spontaneously.

Manual emasculation can also be avoided by the use of chemically induced male sterility in the production of hybrid cotton seed. Chemicals that induce male sterility include gametocides, pollen suppressants, and chemical hybridizing agents. The general procedure is to use a foliar spray before flowering, which inhibits production of viable pollen, but does not injure the pistillate reproductive organs or affect seed development. If the treatment is successful and all of the pollen is killed, self-pollination will not occur in the treated plants, but the flowers will set seed freely from cross-pollination. In such a case, the parent plants used as the male can either not be treated with the chemical agent or can include a genetic factor that causes resistance to the sterilizing effects of the chemical agent. The use of chemically induced male sterility affects fertility in the plants only for the growing season in which the gametocide is applied.

The presence of a male-fertility restorer gene results in the production of a fully fertile $F_1$ hybrid progeny. If no restorer gene is present in the male parent, male-sterile hybrids are obtained. Such hybrids are useful where the vegetative tissue of the cotton plant is used, e.g., for silage, but in most cases, the seeds will be deemed the most valuable portion of the crop, so fertility of the hybrids in these crops must be restored. Therefore, one aspect of the present disclosure relates to cotton variety PX339054W3FE comprising a single gene capable of restoring male fertility in an otherwise male-sterile variety or hybrid plant. Examples of male-sterility genes and corresponding restorers that can be employed within the scope of embodiments of the disclosure are well known to those of skill in the art of plant breeding and are disclosed in, for example, U.S. Pat. Nos. 5,530,191, 5,689,041, 5,741,684, and 5,684,242, the disclosures of which are each specifically incorporated herein by reference in their entirety.

VIII. Cotton Transformation

With the advent of molecular biological techniques that have allowed the isolation and characterization of genes that encode specific protein products, scientists in the field of plant biology developed a strong interest in engineering the genome of plants to contain and to express foreign genes, or additional, or modified versions of native or endogenous genes (perhaps driven by different promoters) to alter the traits of a plant in a specific manner. Such foreign, additional and/or modified genes are referred to herein collectively as "transgenes." The present disclosure, in particular embodiments, also relates to transformed versions of the claimed cotton variety PX339054W3FE containing one or more transgenes.

Plant transformation involves the construction of an expression vector that will function in plant cells. Such a vector comprises DNA comprising a gene under control of or operatively linked to a regulatory element. The expression vector can contain one or more such operably linked gene/regulatory element combinations. The vector(s) can be in the form of a plasmid, and can be used, alone or in combination with other plasmids, to develop transformed cotton plants, using transformation methods as described below to incorporate transgenes into the genetic material of the cotton plant(s).

A. Expression Vectors for Cotton Transformation/Marker Genes

Expression vectors include at least one genetic marker, operably linked to a regulatory element that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts and include, for example, genes that code for enzymes that metabolically detoxify a selective chemical agent that can be an antibiotic or a herbicide, or genes that encode an altered target that is insensitive to the inhibitor. A few positive selection methods are also known in the art. One commonly used selectable marker gene for plant transformation is the neomycin phosphotransferase II (nptII) gene, isolated from a bacterial source, which when placed under the control of plant regulatory signals confers resistance to kanamycin. Fraley et al., *Proc. Natl. Acad. Sci. U.S.A.* 80: 4803 (1983). Another commonly used selectable marker gene is the hygromycin phosphotransferase gene that confers resistance to the antibiotic hygromycin. Vanden Elzen et al., *Plant Mol. Biol.* 5: 299 (1985).

Additional selectable marker genes of bacterial origin that confer resistance to antibiotics include gentamycin acetyl transferase, streptomycin phosphotransferase, aminoglycoside-3'-adenyl transferase and the bleomycin resistance determinant Hayford et al., *Plant Physiol.* 86: 1216 (1988), Jones et al., *Mol. Gen. Genet.* 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or bromoxynil. Comai et al., *Nature* 317: 741-744 (1985), Gordon-Kamm et al., *Plant Cell* 2: 603-618 (1990) and Stalker et al., *Science* 242: 419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, and luciferase. Jefferson, R. A., *Plant Mol. Biol. Rep.* 5: 387 (1987), Teeri et al., *EMBO J.* 8: 343 (1989), Koncz et al., *Proc. Natl. Acad. Sci. U.S.A.* 84: 131 (1987). Another approach to the identification of relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green™, p. 1-4 (1983) and Naleway et al., *J. Cell Biol.* 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP can be used as screenable markers.

B. Promoters

Genes included in expression vectors must be driven by a nucleotide sequence comprising a regulatory element, for example a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissues are referred to as "tissue-specific." A "cell type" specific promoter primarily drives expression in certain cell types in one or more organs, for example vascular cells in roots or leaves. An "inducible" promoter is a promoter that is under environmental control or is induced in response to chemical or hormonal stimuli. Examples of environmental conditions that can effect transcription by inducible promoters include anaerobic conditions or the presence of light. Examples of chemicals that induce expression include salicylic acid and ABA. Tissue-specific, tissue-preferred, cell type specific, and inducible promoters constitute the class of "non-constitutive" promoters. A "constitutive" promoter is a promoter that is active under most environmental conditions and in all cells.

1. Inducible Promoters

An inducible promoter is operably linked to a gene for expression in cotton. Optionally, the inducible promoter is operably linked to a nucleotide sequence encoding a signal sequence that is operably linked to a gene for expression in cotton. With an inducible promoter the rate of transcription increases in response to an inducing agent. Any inducible promoter can be used in embodiments of the instant disclosure. A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone.

2. Constitutive Promoters

A constitutive promoter is operably linked to a gene for expression in cotton or is operably linked to a nucleotide sequence encoding a signal sequence that is operably linked to a gene for expression in cotton. Many different constitutive promoters can be used in embodiments of the present disclosure. Exemplary constitutive promoters include, but are not limited to, the promoters from plant viruses such as the 35S promoter from CaMV and the promoters from such genes as rice actin, maize ubiquitin, and corn H3 histone. Also, the ALS promoter, an XbaI/NcoI fragment 5' to the *Brassica napus* ALS3 structural gene (or a nucleotide sequence that has substantial sequence similarity to the XbaI/NcoI fragment) represents a particularly useful constitutive promoter.

3. Tissue-Specific or Tissue-Preferred Promoters

A tissue-specific promoter is operably linked to a gene for expression in cotton. Optionally, the tissue-specific promoter is operably linked to a nucleotide sequence encoding a signal sequence that is operably linked to a gene for expression in cotton. Plants transformed with a gene of interest operably linked to a tissue-specific promoter produce the protein product of the transgene exclusively, or preferentially, in a specific tissue. Any tissue-specific or tissue-preferred promoter can be utilized in embodiments of the instant disclosure. Exemplary tissue-specific or tissue-preferred promoters include, but are not limited to, a seed-preferred promoter such as that from the phaseolin gene; a leaf-specific and light-induced promoter such as that from cab or rubisco; an anther-specific promoter such as that from LAT52; a pollen specific promoter such as that from Zm13; or a microspore-preferred promoter such as that from apg.

C. Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by operably linking the nucleotide sequence encoding a signal sequence to the 5' and/or 3' region of a gene encoding the protein of interest. Targeting sequences at the 5' and/or 3' end of the structural gene can determine, during protein synthesis and processing, where the encoded protein is ultimately compartmentalized. The presence of a signal sequence directs a polypeptide to either an intracellular organelle or subcellular compartment or for secretion to the apoplast. Use of any signal sequence known in the art is contemplated for use in embodiments of the present disclosure.

D. Foreign Protein Genes and Agronomic Genes

Using transgenic plants of embodiments of the present disclosure, a foreign protein can be produced in commercial quantities. Thus, techniques for the selection and propagation of transformed plants, which are well understood in the art, yield a plurality of transgenic plants, which are harvested in a conventional manner, and a foreign protein then can be extracted from a tissue of interest or from total biomass. Protein extraction from plant biomass can be accomplished by known methods.

According to a preferred embodiment, the transgenic plant provided for commercial production of foreign protein is cotton. In another preferred embodiment, the biomass of interest is seed. For the relatively small number of transgenic plants that show higher levels of expression, a genetic map can be generated, for example via conventional Restriction Fragment Length Polymorphisms (RFLP), Polymerase Chain Reaction (PCR) analysis, and Simple Sequence Repeats (SSR), in a manner that identifies the approximate chromosomal location of the integrated DNA molecule. For exemplary methodologies in this regard, see Glick and Thompson, Methods in Plant Molecular Biology and Biotechnology 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. In particular embodiments, map comparisons can involve, for example, hybridizations, RFLP, PCR, SSR and sequencing, all of which are conventional techniques.

Likewise, in accordance with embodiments of the present disclosure, agronomic genes can be expressed in transformed plants. More particularly, plants can be genetically engineered to express various phenotypes of agronomic interest. Exemplary genes implicated in this regard include, but are not limited to:

1. Genes that Confer Resistance to Pests or Disease and that Encode:

(a) Plant disease resistance genes. Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains. See, for example, Jones et al., Science 266: 789 (1994) (cloning of the tomato Cf-9 gene for resistance to *Cladosporium flavum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*).

(b) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998.

(c) A lectin. See, for example, the disclosure by Van Damme et al., Plant Molec. Biol. 24: 25 (1994), who disclose the nucleotide sequences of several *Clivia miniata* mannose-binding lectin genes.

(d) A vitamin-binding protein such as avidin. See PCT application US93/06487, the contents of which are hereby incorporated by reference in their entirety. The application teaches the use of avidin and avidin homologues as larvicides against insect pests.

(e) An enzyme inhibitor, for example, a protease inhibitor or an amylase inhibitor. See, for example, Abe et al., J. Biol. Chem. 262: 16793 (1987) (nucleotide sequence of rice cysteine proteinase inhibitor), Huub et al., Plant Molec. Biol. 21: 985 (1993) (nucleotide sequence of cDNA encoding tobacco proteinase inhibitor I), and Sumitani et al., Biosci. Biotech. Biochem. 57: 1243 (1993) (nucleotide sequence of *Streptomyces nitrosporeus* α-amylase inhibitor).

(f) An insect-specific hormone or pheromone such as an ecdysteroid or juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(g) An insect-specific peptide or neuropeptide that, upon expression, disrupts the physiology of the affected pest. For example, see the disclosures of Regan, J. Biol. Chem. 269: 9 (1994) (expression cloning yields DNA coding for insect diuretic hormone receptor), and Pratt et al., Biochem. Biophys. Res. Comm 163: 1243 (1989) (an allostatin is identified in *Diploptera puntata*). See also U.S. Pat. No. 5,266,317 to Tomalski et al., who disclose genes encoding insect-specific, paralytic neurotoxins.

(h) An insect-specific venom produced in nature by a snake, a wasp, etc. For example, see Pang et al., Gene 116: 165 (1992), for disclosure of heterologous expression in plants of a gene coding for a scorpion insectotoxic peptide.

(i) An enzyme responsible for a hyperaccumulation of a monoterpene, a sesquiterpene, a steroid, hydroxamic acid, a phenylpropanoid derivative or another non-protein molecule with insecticidal activity.

(j) An enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, whether natural or synthetic. See PCT application WO 93/02197 in the name of Scott et al., which discloses the nucleotide sequence of a callase gene. DNA molecules that contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene.

(k) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a corn calmodulin cDNA clone.

(l) A hydrophobic moment peptide. See PCT application WO95/16776 (disclosure of peptide derivatives of Tachyplesin that inhibit fungal plant pathogens) and PCT application WO95/18855 (teaches synthetic antimicrobial peptides that confer disease resistance), the respective contents of which are hereby incorporated by reference in their entirety.

(m) A membrane permease, a channel former or a channel blocker. For example, see the disclosure by Jaynes et al., Plant Sci. 89: 43 (1993), of heterologous expression of a cecropin-β lytic peptide analog to render transgenic tobacco plants resistant to *Pseudomonas solanacearum*.

(n) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(o) An insect-specific antibody or an immunotoxin derived therefrom. Thus, an antibody targeted to a critical metabolic function in the insect gut will inactivate an affected enzyme, killing the insect. Cf. Taylor et al., Abstract #497, Seventh Intl. Symposium on Molecular Plant-Microbe Interactions (Edinburgh, Scotland (Edinburgh, Scotland, 1994) (enzymatic inactivation in transgenic tobacco via production of single-chain antibody fragments).

(p) A virus-specific antibody. See, for example, Tavladoraki et al, Nature 366: 469 (1993), who show that transgenic plants expressing recombinant antibody genes are protected from virus attack.

(q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonate. See Lamb et al., Bio/Technology 10: 1436 (1992). The cloning and characterization of a gene that encodes a bean endopolygalacturonase-inhibiting protein is described by Toubart et al., Plant J. 2: 367 (1992).

(r) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

2. Genes that Confer Resistance to a Herbicide, for Example:

(a) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241 (1988), and Miki et al., Theor. Appl. Genet. 80: 449 (1990), respectively.

(b) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxypropionic acids and cyclohexones (ACCase inhibitor-encoding genes). See, for example, U.S. Pat. No. 4,940,835 to Shah et al., which discloses the nucleotide sequence of a form of EPSP that can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes that confer resistance to herbicides such as L-phosphinothricin. The nucleotide sequence of a phosphinothricin-acetyl-transferase gene is provided in European application No. 0 242 246 to Leemans et al. Furthermore, De Greef et al., Bio/Technology 7: 61 (1989), describe the production of transgenic plants that express chimeric bar genes coding for phosphinothricin acetyl transferase activity. Exemplary of genes conferring resistance to phenoxypropionic acids and cyclohexones, such as sethoxydim and haloxyfop, are the Acc1-S1, Acc1-S2 and Acc1-S3 genes described by Marshall et al., Theor. Appl. Genet. 83: 435 (1992).

(c) A herbicide that inhibits photosynthesis, such as a triazine (psbA and gs+ genes) or a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

3. Genes that Confer or Contribute to a Value-Added Trait, Such as:

(a) Modified fatty acid metabolism, for example, by transforming a plant with an antisense gene of stearoyl-ACP desaturase to increase stearic acid content of the plant. See Knultzon et al., Proc. Natl. Acad. Sci. USA 89: 2624 (1992).

(b) Decreased phytate content:

(i) Introduction of a phytase-encoding gene will enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene.

(ii) A gene can be introduced that reduces phytate content. In cotton, this, for example, can be accomplished by cloning and then reintroducing DNA associated with the single allele that is responsible for cotton mutants characterized by low levels of phytic acid. See Raboy et al., Maydica 35: 383 (1990).

(iii) Modified carbohydrate composition effected, for example, by transforming plants with a gene coding for an enzyme that alters the branching pattern of starch. See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtillus* levansucrase gene), Pen et al., Bio/Technology 10: 292 (1992) (production of transgenic plants that express *Bacillus licheniformis* α-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley α-amylase gene), and Fisher et al., Plant Physiol. 102: 1045 (1993) (corn endosperm starch branching enzyme II).

E. Methods for Cotton Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, inc., Boca Raton, 1993) pages 89-119.

1. *Agrobacterium*-Mediated Transformation

One method for introducing an expression vector into plants is based on the natural transformation system of *Agrobacterium*. See, for example, Horsch et al., Science 227: 1229 (1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant. Sci. 10: 1 (1991). Descriptions of *Agrobacterium* vector systems and methods for *Agrobacterium*-mediated gene transfer are provided by Gruber et al., supra, Miki et al., supra, and Moloney et al., Plant Cell Reports 8: 238 (1989). See also U.S. Pat. No. 5,591,616, issued Jan. 7, 1997.

2. Direct Gene Transfer

Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm (See e.g., U.S. Pat. Nos. 5,550,318; 5,736,369; 5,538,880; and PCT Publication WO 95/06128). The expression vector is introduced into plant tissues with a biolistic device that accelerates the microprojectiles to speeds of 300 to 600 m/s, which is sufficient to penetrate plant cell walls and membranes. Sanford et al, Part. Sci. Technol. 5: 27 (1987), Sanford, J. C., Trends Biotech. 6: 299 (1988), Klein et al., Bio/Technology 6: 559-563 (1988), Sanford, J. C., Physiol. Plant 79: 206 (1990), Klein et al., Biotechnology 10: 268 (1992).

Another method for physical delivery of DNA to plants is sonication of target cells. Zhang et al., Bio/Technology 9: 996 (1991). Alternatively, liposome or spheroplast fusion have been used to introduce expression vectors into plants. Deshayes et al., EMBO J., 4: 2731 (1985), Christou et al., Proc. Natl. Acad. Sci. U.S.A. 84: 3962 (1987). Direct uptake of DNA into protoplasts using $CaCl_2$ precipitation, polyvinyl alcohol or poly-L-ornithine have also been reported. Hain et al., Mol. Gen. Genet. 199: 161 (1985) and Draper et al., Plant Cell Physiol. 23: 451 (1982). Electroporation of protoplasts and whole cells and tissues have also been described. U.S. Pat. No. 5,384,253 and Donn et al; in Abstracts of VIIth International Congress on Plant Cell and Tissue Culture IAPTC, A2-38, p 53 (1990); D'Halluin et al., Plant Cell 4: 1495-1505 (1992) and Spencer et al., Plant Mol. Biol. 24: 51-61 (1994).

Other methods that have been described for the genetic transformation of cotton include electrotransformation (U.S. Pat. No. 5,371,003) and silicon carbide fiber-mediated transformation (U.S. Pat. Nos. 5,302,532 and 5,464,765).

Following transformation of cotton target tissues, expression of the above-described selectable marker genes allows for preferential selection of transformed cells, tissues and/or plants, using regeneration and selection methods now well known in the art.

The foregoing methods for transformation are typically used for producing transgenic cotton varieties. Transgenic cotton varieties can then be crossed, with another (non-transformed or transformed) cotton variety, to produce a transgenic hybrid cotton plant. Alternatively, a genetic trait that has been engineered into a particular cotton variety using the foregoing transformation techniques can be moved into another line using traditional backcrossing techniques that are well known in the plant breeding arts. For example, a backcrossing approach can be used to move an engineered trait from a public, non-elite line into an elite line, or from a hybrid cotton plant containing a foreign gene in its genome into a line or lines that do not contain that gene.

IX. Genetic Complements

In addition to phenotypic observations, a plant can also be described by its genotype. The genotype of a plant can be described through a genetic marker profile that can identify plants of the same variety, a related variety or be used to determine or to validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), which are also referred to as Microsatellites, and Single Nucleotide Polymorphisms (SNPs), Isozyme Electrophoresis and Isoelectric Focusing.

Particular markers used for these purposes are not limited to the set of markers disclosed herewithin, but are envisioned to include any type of genetically stable marker and marker profile that provides a way of distinguishing varieties. In addition to being used for identification of cotton varieties, a hybrid produced through the use of PX339054W3FE, and identification or verification of the pedigree of progeny plants produced through the use of PX339054W3FE, the genetic marker profile is also useful in breeding and developing backcross conversions.

Methods of generating genetic marker profiles using SSR polymorphisms are well known in the art. SSRs are genetic markers based on polymorphisms in repeated nucleotide sequences, such as microsatellites. The phrase "simple sequence repeats" or "SSR" refers to di-, tri- or tetra-nucleotide repeats within a genome. The repeat region can vary in length between genotypes while the DNA flanking the repeat is conserved, such that the primers will work in a plurality of genotypes. A polymorphism between two genotypes represents repeats of different lengths between the two flanking conserved DNA sequences. A marker system based on SSRs can be highly informative in linkage analysis relative to other marker systems in that, in some embodiments, multiple alleles are present. Another advantage of this type of marker is that, through use of flanking primers, detection of SSRs can be achieved, for example, by the polymerase chain reaction (PCR). The PCR detection is done by the use of two oligonucleotide primers flanking the polymorphic segment of repetitive DNA followed by DNA amplification. This step involves repeated cycles of heat denaturation of the DNA followed by annealing of the primers to their complementary sequences at low temperatures, and extension of the annealed primers with DNA polymerase. Size separation of DNA fragments on agarose or polyacrylamide gels following amplification comprises the major part of the methodology.

DNA isolation and amplification can be performed in certain embodiments of the present disclosure as follows. DNA can be extracted from plant leaf tissue using DNeasy 96 Plant Kit from Qiagen, Inc. (Valencia, Calif., U.S.A.) following an optimized September 2002 manufacturer's protocol. PCR amplifications are performed using a Qiagen HotStar™ Taq master mix in an 8 µl reaction format as follows: 2 µl DNA (5 ng/µL+6 µL of master mix). The PCR conditions are as follows: 12 mins. at 95° C., 40 cycles of 5 seconds at 94° C., 15 seconds at 55° C., 30 seconds at 72° C., 30 mins at 72° C., followed by cooling to 4° C. Following isolation and amplification, markers can be scored by gel electrophoresis of the amplification products. Scoring of marker genotype is based on the size of the amplified fragment as measured by molecular weight (MW) rounded to the nearest integer. Multiple samples, comprising fluorescently labeled DNA fragments, can be processed in an ABI 3700 capillary-based machine and precise allele sizing and locus genotyping can be done by running GeneScan and Genotyper software (PE *Applied Biosystems*, Foster City, Calif.). When comparing varieties, it is preferable that all SSR profiles be performed in the same lab. An SSR service is available to the public on a contractual basis by Paragen, Research Triangle Park, N.C. (formerly Celera AgGen of Davis, Calif.).

All publications, patents and patent applications mentioned in the specification are indicative of the level of those skilled in the art to which this disclosure pertains. All such publications, patents and patent applications are incorporated by reference herein to the same extent as if each was specifically and individually indicated to be incorporated by reference herein.

The foregoing invention has been described in some detail by way of illustration and example for purposes of clarity and understanding. However, it will be appreciated by those having ordinary skill in the art that certain changes and modifications such as single gene modifications and mutations, somoclonal variants, variant individuals selected from large populations of the plants of the instant variety and the like can be practiced within the scope of the embodiments of the invention, as limited only by the scope of the appended claims, without departing from the true concept, spirit, and scope of the invention.

What is claimed is:

1. A seed of cotton variety designated PX339054W3FE, or a regenerable part thereof, representative seed of the variety having been deposited under ATCC Accession No. PTA-123652 on Nov. 15, 2016.

2. A part of the seed of claim 1 selected from the group consisting of hull, germ and endosperm.

3. The seed of claim 1, further comprising a coating.

4. A population of cotton seeds comprising the cotton seed of claim 1.

5. A method for producing a seed of a cotton plant, the method comprising:

(a) planting the seed of claim 1 in proximity to a second seed of claim 1 or to a cotton seed from a different variety;
(b) growing a plant from the seed of claim 1 under pollinating conditions; and,
(c) harvesting cotton seed from the plant grown from the seed of claim 1.

6. A cotton seed produced by the method of claim 5.

7. The method of claim 5, further comprising pre-treating the seed before performing step (a).

8. The method of claim 5, further comprising treating the growing plant or soil surrounding the growing plant with an agricultural chemical.

9. A cotton plant produced by growing the seed of claim 1.

10. A regenerable part of the cotton plant of claim 9, selected from the group consisting of an intact plant cell, a plant protoplast, embryos, pollen, flowers, seeds, pods, gossypol glands, leaves, bolls, stems, roots, root tips, and anthers.

11. A cotton plant, or a regenerable part thereof, wherein said plant has all the physiological and morphological characteristics of the cotton plant of claim 9.

12. A population of cotton plants comprising the cotton plant of claim 9.

13. The population of cotton plants of claim 12, wherein the population is present in a field and the population further comprises other, different cotton plants.

14. A method for producing a cotton plant, comprising:
(a) crossing cotton variety plant PX339054W3FE, representative seed of the variety having been deposited under ATCC Accession No. PTA-123652 on Nov. 15, 2016, with another different cotton plant to yield progeny cotton seed.

15. The method of claim 14, wherein the other, different cotton plant is a cotton variety.

16. The method of claim 14, further comprising:
(b) growing the progeny cotton seed from step (a) under self-pollinating or sib-pollinating conditions for about 5 to about 7 generations; and
(c) harvesting resultant seed.

17. The method of claim 14, further comprising selecting plants obtained from growing at least one generation of the progeny cotton seed for a desirable trait.

18. A method of introducing a desired trait into cotton variety PX339054W3FE, representative seed of the variety having been deposited under ATCC Accession No. PTA-123652 on Nov. 15, 2016, comprising:
(a) crossing PX339054W3FE plants with plants of another cotton variety that comprise a desired trait to produce F1 progeny plants;
(b) selecting F1 progeny plants that have the desired trait;
(c) crossing selected progeny plants with PX339054W3FE plants to produce backcross progeny plants;
(d) selecting for backcross progeny plants that comprise the desired trait and physiological and morphological characteristics of cotton variety PX339054W3FE; and
(e) performing steps (c) and (d) one or more times in succession to produce selected or higher backcross progeny plants that comprise the desired trait and all of the physiological and morphological characteristics of cotton variety PX339054W3FE listed in Table 1 as determined at the 5% significance level when grown in the same environmental conditions.

* * * * *